(12) United States Patent
Gourdeau et al.

(10) Patent No.: US 7,763,604 B2
(45) Date of Patent: *Jul. 27, 2010

(54) METHODS FOR ADMINISTRATION OF A FARNESYL DIBENZODIAZEPINONE

(75) Inventors: Henriette Gourdeau, Montreal (CA); Maxime Ranger, Montreal (CA); François Berger, Meylan (FR); Bryan Simard, Montreal (CA)

(73) Assignee: Thallion Pharma Ceuticals, Inc., Montreal (CA)

( * ) Notice: Subject to any disclaimer, the term of this patent is extended or adjusted under 35 U.S.C. 154(b) by 506 days.

This patent is subject to a terminal disclaimer.

(21) Appl. No.: 11/434,154

(22) Filed: May 16, 2006

(65) Prior Publication Data

US 2006/0270662 A1  Nov. 30, 2006

Related U.S. Application Data

(63) Continuation-in-part of application No. 11/130,295, filed on May 16, 2005, now Pat. No. 7,358,241.

(51) Int. Cl.
*A61K 31/5513* (2006.01)
*A61P 35/00* (2006.01)

(52) U.S. Cl. ..................................... 514/220
(58) Field of Classification Search .................. 514/220
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 5,039,660 A | 8/1991 | Leonard | |
| 5,541,181 A | 7/1996 | Ohkuma et al. | 514/220 |
| 2003/0109518 A1 | 6/2003 | Lu et al. | 514/221 |
| 2003/0219718 A1 | 11/2003 | Weber et al. | 435/4 |
| 2004/0220179 A1 | 11/2004 | Lu et al. | 514/217.03 |
| 2006/0079509 A1 | 4/2006 | McAlpine | |

FOREIGN PATENT DOCUMENTS

| | | |
|---|---|---|
| CA | 2248820 | 9/1997 |
| CA | 2 507 567 | 11/2005 |
| CA | 2 544 381 | 7/2006 |
| EP | 1 733 758 | 12/2006 |
| WO | WO 2004/065591 A1 | 8/2004 |
| WO | WO 2006/034567 A | 4/2006 |

OTHER PUBLICATIONS

Alberts et al., "Molecular Biology of the Cell (3rd Edition)," Garland Publishing, Inc., 1994, pp. 1255-1294.

Anderson et al., "Cancer Chemotherapy and Infusional Scheduling," Oncology, 8(5), 1994, pp. 99-111.

E. T. Beck, "Unknotting the Complexities of Multidrug Resistance: the Involvement of DNA Topoisomerases in Drug Action and Resistance," J. Natl. Cancer Inst. 81(22), 1989, pp. 1683-1685.

Berge et al., "Pharmaceuticals Salts," Journal of Pharmaceutical Sciences, 66(1), 1977, pp. 1-19.

Bono et al., "Peripheral Benzodiazepine Receptor Agonists Exhibit Potent Antiapoptotic Activities," Biochem. Biophys. Res. Comm., 265(2), 1999, pp. 457-461.

"United Kingdom Coordinating Committee on Cancer Research (UKCCCR) Guidelines for the Welfare of Animals in Experimental Neoplasia (second edition)," British Journal of Cancer, 1998, 77(1), pp. 1-11.

Broaddus et al., "Peripheral-type Benzodiazepine Receptors in Human Glioblastomas: Pharmacologic Characterization and Photoaffinity Labeling of Ligand Recognition Site," Brain Research, 518, 1990, pp. 199-208.

Carayon et al., "Involvement of Peripheral Benzodiazepine Receptors in the Protection of Hematopoietic Cells Against Oxygen Radical Bcl-2-mediated Cytoprotection," Blood, 87(8), 1995, pp. 3170-3178.

Charan et al., "A New Antimicrobial Alkaloid from a Micromonospora sp.," Abstract and Figures from Poster Presentation #p:157 at the 44th Annual Meeting of the American Society of Pharmacognosy, Chapel Hill, N.C., Jul. 12-16, 2006.

Charan et al., "Diazepinomicin, a New Antimicrobial Alkaloid from a Marine Micromonospora sp.," Journal of Nat. Prod. 67(8), Aug. 2004, pp. 1431-1433.

Chelli et al., "Peripheral Benzodiazepine Receptor Ligands: Mitochondrial Transmembrane Potential Depolarization and Apoptosis Induction in Rat C6 Glioma Cells," Biochemical Pharmacology, 68, 2004, pp. 125-134.

S. Childs, "The MDR Superfamily of Genes and its Biological Implication," Imp. Adv. Oncol., 1994, pp. 21-36.

Cole et al., "Overexpression of a Transporter gene in a Multidrug-resistance Human Lung Cancer Cell Line," Science, 258, 1992, pp. 1650-1654.

Craig et al., Modern Pharmacology, 4th Edition 1994, Little, Brown and Company, pp. 669-670.

(Continued)

*Primary Examiner*—Bruck Kifle
(74) *Attorney, Agent, or Firm*—Roylance Abrams

(57) ABSTRACT

This invention relates to methods of inhibiting growth and/or proliferation of a neoplastic cell, and methods of treating neoplasms by administration of the farnesylated dibenzodiazepinone compound of Formula I via continuous intravenous infusion. The invention includes pharmaceutical compositions comprising the compound of Formula I:

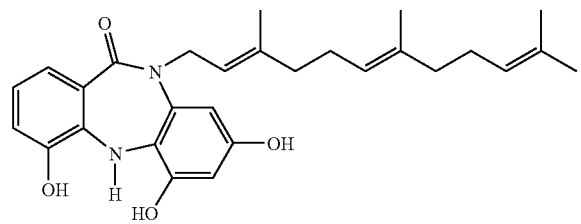

48 Claims, 13 Drawing Sheets

OTHER PUBLICATIONS

Damm et al., "[3H] Flunitrazepam: its Advantages as a Ligand for the Idenficiation of Benzodiazepine Receptors in Rat Brain Membranes," Res. Comm. Chem. Pathol. Pharmacol., 22, 1978, pp. 597-600.

Decaudin et al., "Peripheral Benzodiazepine Receptor Ligands Reverse Apoptosis Resistance of Cancer Cells in vitro and in vivo," Cancer Research, 62(5), 2002, pp. 1388-1393.

DeGeorge et al., "Regulatory Considerations for Preclinical Development of Anticancer Drugs," Cancer Chemother. Pharmacol., 41, 1998, pp. 173-185.

Embley et al., "The Molecular Phylogeny and Systematics of the Actinomycetes," Annu. Rev. Microbiol., 48, 1994, pp. 257-289.

Fan D. et al., "Reversal of Multidrug Resistance in Cancer," ed. Kellen, J.A., 1993, pp. 93-125.

Freireich et al., "Quantitative Comparison of Toxicity of Anticancer Agents in Mouse, Rat, Hamster, Dog, Monkey, and Man," Cancer Chemother. Reports, 50(4), 1966, pp. 219-244.

M. Goodfellow, "Suprageneric Classification of Actinomycetes," Bergey's Manual of Systematic Bacteriology, 4, 1989, pp. 2322-2339.

Greidanus et al., "Continuous Infusion of Low-dose Doxorubicin, Epirubicin and Mitoxantrone in Cancer Chemotherapy: A Review," Pharm. Weekbl. Sci., 10(6), 1998, pp. 237-245.

Guo et al, "Targeted Delivery of a Peripheral Benzodiazepine Receptor Ligand-Gemcitabine Conjugate to Brain Tumors n a Xenograft Model," Cancer Chemother. Pharmacol. 48(2), 2001, pp. 169-176.

Healing et al., Handbook of Pre-clinical Continuous Intravenous Infusion, 2000, Taylor & Francis.

Hirsch et al., "PK11195, a Ligand of the Mitochondrial Benzodiazepine Receptor, Facilitates the Induction of Apoptosis and Reverses Bcl-2-Mediated Cytoprotection," Experimental Cell Research, 241(2), 1998, pp. 426-434.

Igarashi et al., "Revision of the Structure Assigned to the Antibiotic BU-4664L from Micromonopora," Journal of Antibiotics, 58(7), 2005, pp. 350-352.

Correction to p. 352 Igarashi et al., "Revision of the Structure Assigned to the Antibiotic BU-4664L from Micromonopora," Journal of Antibiotics, 58(7), 2005, pp. 350-352.

Jakubikova et al., "PK11195, An Isoquinoline Carboxamide Ligand of the Mitochondrial Benzodiazepine Receptor, Increased Drug Uptake and Facilitated Drug-induced Apoptosis in Human Multidrug-Resistant Leukemia Cells in vitro," Neoplasma, 49(4), 2002, pp. 231-236.

Katz et al., "Increased Density of Peripheral Benzodiazepine-binding sites in Ovarian Carcinomas as Compared with Benign Ovarian Tumours and Normal Ovaries," Clin. Sci., 78(2), 1990, pp. 155-158.

Katz et al., "Increase in Peripheral Benzodiazepine Binding Sites in Colonic Adenocarcinoma," Oncology, 47(2), 1990, pp. 139-142.

Kupczyk-Subotkowska et al, "Modulation of Melphalan Resistance in Glioma Cells in a Peripheral Benzodiazepine Receptor Ligand-Melphalan Conjugate," J. Med. Chem., 40(11), 1997, pp. 1726-1730.

Landau et al., "Antiproliferative and Differentiating Effects of Benzodiazepine Receptor Ligands on B16 Meanoma Cells," J. Biochem. Pharmacol., 56(8) 1998, pp. 1029-1034.

L. Lash, "The Mitochondrial Benzodiazepine Receptor as a Potential Target Protein for Drug Development: Demonstration of Functional Significance with Cell Lines Exhibiting Differential Expression of Bcl-2," Toxicological Sciences, 74, 2003, pp. 1-3.

LeFur et al., "Differentiation Between Two Ligands for Peripheral Benzodiazepine Binding Sites, [3H]R05-4864 and [3H]PK 11195, by Thermodynamic Studies," Life Sci. USA, 33(5), 1983, pp. 449-457.

Miettinen et al., "Expression of Peripheral-type Benzodiazepinone Receptor and Diazepam Binding Inhibitor in Human Astrocytomas: Relationship to Cell Proliferation," Cancer Res., 55(12), 1995, pp. 2691-2695.

Pawlikowski et al., "Inhibition of Cell Profieration of Human Gliomas by Benzodiazepines in vitro," Acta Neurol. Scand. 1988, 77(3) pp. 231-233.

Premont et al., "[3H] Norepinephrine Binding by Rat Glial Cells in Culture. Lack of Correlation Between Binding and Adenylate Cyclase Activiation," Biochem Biophys. Acta., 381(2), 1975, pp. 368-375.

Rooseboom et al., "Enzyme-Catalyzed Activiation of Anticancer Prodrugs," Pharmacol. Reviews, 56, 2004, pp. 53-102.

Scheffer et al., "The Drug Resistance-related Protein LRP is the Human Major Vault Protein," Nat. Med., 1(6), 1995, pp. 578-582.

Speth et al., "Benzodiazepine Receptors: Temperature Dependence of [H3] Flunitrazepam Binding," Life Sci., 24(4), 1979, pp. 351-357.

Stoebner et al., "Transient Protection by Peripheral Benzodiazepine Receptors During the Early Events of Ultraviolet Light-induced Apoptosis," Cell Death Differ., 8(7), 2001, pp. 747-753.

Venturini et al., "Increased Expression of Peripheral Benzodiazepine Receptors and Diazepam Binding Inhibitor in Human Tumors Sited in the Liver," Life Sci., 65(21), 1999, pp. 2223-2231.

Verma et al., "Photodynamic Tumor Therapy: Mitochondrial Benzodiazepine Receptors as a Therapeutic Target," Mol. Med., 4(1), 1998, pp. 40-45.

Wang et al., "Benzodiazepines that Bind at Peripheral Sites Inhibit Cell Proliferation," Proc. Natl. Acad. Sci. USA, 81, 1984, pp. 753-756.

Workman et al., "United Kingdom Co-ordinating Committee on Cancer Research (UKCCCR) Guidelines for the Welfare of Animals in Experimental Neoplasmia (Second Edition)," British Journal of Cancer, 77, 1998, pp. 1-10.

J.A. Wils, "High-Dose Infusional 5-FU in the Treatment of Advanced Colorectal Cancer: A Summary of the European Experience," J. Infus. Chemotherapy, 6(3), 1996, pp. 145-148.

Dimitradou et al., "Identification and Characterization of a New Cytotoxic Agent from Actinomycetes (ECO-04601)," 95th AACR Annual Meeting, Mar. 27-31, 2004, p. 2060.

Dimitradou et al., "A New Antitumor Compound, ECO-4601: Preclinical Evaluation and in vivo Efficacy in Glioma," 16th EORTC-NCI-AACR Symposium, Sep. 28-Oct. 1, 2004, p. 569.

Simard et al., "ECO-4601, A Novel Anticancer Compound, is a Peripheral Benzodiazepine Receptor Ligand and Induces Apoptosis in Gliomas," 96th AACR Annual Meeting, Apr. 16-20, 2005, p. 5896.

Press Release—"Ecopia's Cancer Drug Candidate Effective Against Brain Tumour in a Preclinical Model," Ecopia BioSciences Inc., Montreal, Quebec, Feb. 2, 2004, pp. 29-30.

Industry Canada, Life Science New Briefs, 3(46), Feb. 11, 2004, pp. 1-4.

Healing et al., "Handbook of Pre-clinical Continuous Intravenous Infusion," Taylor & Francis, 2000, pp. 1-330.

J. Lokich et al., "*Dose Intensity for Bolus versus Infusion Chemotherapy Administration: Review of the Literature of 27 Antineoplastic Agents,*" Annals of Oncology, 1997, 8(1), p. 15-25.

International Search Report from corresponding application PCT/CA2007/000886.

Antitumor efficacy of the compound of Formula I against orthotopic C6 glioma tumor xenograft Days After Tumor Cell Inoculation

METHODS FOR ADMINISTRATION OF A FARNESYL DIBENZODIAZEPINONE

RELATED APPLICATIONS

This application claims benefit under 35 U.S.C. 120 as a continuation-in-part of U.S. application Ser. No. 11/130,295, filed May 16, 2005, now U.S. Pat. No. 7,358,241, the entire teachings of which are incorporated herein by reference for all purposes.

FIELD OF INVENTION

This invention relates to compositions and methods for inhibiting growth and proliferation of a neoplastic cell, and methods of treating neoplasms in a mammal using the compound of Formula I or a pharmaceutically acceptable salt, prodrug thereof. More particularly, the invention relates to the use of the compound of Formula I as a continuous intravenous infusion administrable preparation for the treatment of neoplastic disorders.

BACKGROUND

Neoplasia occurs when normal body cells are changed, proliferating without regard to normal cellular restraints, and invade and colonize areas of the body normally occupied by other cells. See B. Alberts et al., *Molecular Biology of the Cell* 1255-1294 (3d ed. 1994). According to the American Cancer Society, one-half of American men and one-third of American women will at some point in their lives develop a neoplastic disorder.

Abnormal cell proliferation is usually characterized by an increase rate of division and in some cases uncontrolled growth. One example of a proliferative cell disorder is a tumor or neoplasm. In addition to posing a serious risk in and of themselves, primary malignant neoplasms are particularly problematic given their tendency to invade surrounding tissues and metastasize to distant organs in the body. To date, the most frequently used methods for treating neoplasia, include surgical procedures, radiation therapy, and drug therapies, and combinations of the foregoing. These methods involve significant risk (e.g., of infection, death) to the patient. More importantly, the probability of eliminating all malignant cells is small, particularly if the zone of the malignant growth is not well defined or if the primary tumor has metastasized by the time of surgery. Achieving therapeutic doses effective for treating neoplasm is often limited by the toxic side effects of the anti-cancer agent on normal, healthy tissue. An ideal anti-cancer agent has tissue specificity, thereby reducing side-effects on normal (dividing) cells. There is a need in the art for novel cancer therapeutics which have higher efficacy, specificity, or reduced side effects.

Current antineoplastic drug therapies are administered via a wide variety of routes, and are mostly given orally or by bolus intravenous injection or short infusion, i.e. mostly for up to about 60 minutes. The frequency of the administration generally ranges from once daily to once every week. Other less frequently used modes of administrations include regional intraarterial perfusion, intracavitary, intrathecal, intraventricular, intravesical and topical (Craig et al., *Modern pharmacology* 4th edition (1994), Little, Brown and Co, page 669-670). In 1994, continuous intravenous infusion was considered investigational (Anderson and Lokich (1994), Oncology, 8(5), p 99-111), with rare exceptions, including 5-FU (Wils (1996), *J. Infus. Chemother.*, vol 6, no 3, 145-148). Intravenous bolus (or short infusion) and continuous infusion (CIV) modes of administration of several drugs were tested and compared and in many cases there was no advantage with CIV administration compared to i.v. bolus administration (Anderson and Lokich, supra).

The compound of Formula I (see below) was disclosed in CA 2,466,340, incorporated by reference in its entirety, and was shown to possess a broad spectrum of anticancer activity by in vitro testing. Both this application and a poster presentation (poster 569, 16th EORTC-NCI-AACR Symposium—Geneva, Sept. 28 to Oct. 1, 2004) disclosed in vivo activity following intraperitoneal administration in glioma mouse models, as well as PK and toxicity profiles including intravenous (IV) bolus, intraperitoneal (IP) and oral (PO) administration. Following the toxicity profile, the AACR poster suggested IV bolus dosing to be the preferred route of administration. The compound was further disclosed in Charan et al. (2004), *J. Nat. Prod.*, vol 67, 1431-1433 as an antimicrobial agent, and in Igarashi et al. (2005), *J. Antibiot.*, vol 58, no 5, 350-352.

SUMMARY OF THE INVENTION

In one aspect, the invention provides a novel method for the administration of the compound of Formula I, or a pharmaceutically acceptable prodrug of the compound of Formula I: comprising the step of administering by a continuous intravenous infusion, a therapeutically effective amount of the compound of Formula I to a patient in need thereof. In one embodiment, the continuous intravenous infusion is given for at least 8 hours per day, over a period of 1 to 28 days, preferably from 7 to 14 days. In another embodiment, the continuous intravenous infusion is given 24 hours per day over a period of 1 to 28 days, preferably from 7 to 14 days.

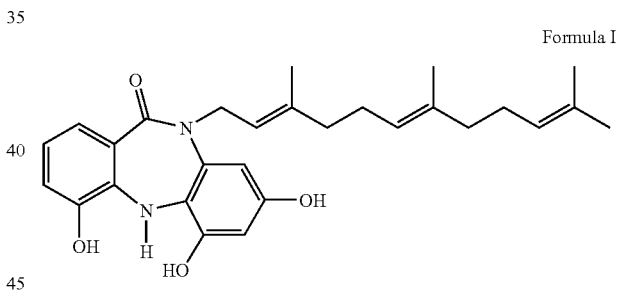

Formula I

In another aspect, the invention provides a method of treating a neoplasm in a mammal, comprising the step of administering by continuous intravenous infusion to the mammal, a therapeutically effective amount of the compound of Formula I, or a pharmaceutically acceptable prodrug of the compound of Formula I, such that the neoplasm is treated.

In another aspect, the invention provides a method of inducing apoptosis of a neoplasm in a mammal, comprising the step of administering by continuous intravenous infusion to the mammal a therapeutically effective amount of the compound of Formula I, or a pharmaceutically acceptable prodrug, such that the neoplasm is treated or controlled.

In another aspect, the invention provides use of a continuous intravenous infusion dosage of the compound of Formula I, or a pharmaceutically acceptable prodrug thereof, for the inhibition of the growth or proliferation of a neoplastic cell in a mammal. In another embodiment, the invention provides use of a continuous intravenous infusion dosage of the compound of Formula I, or a pharmaceutically acceptable prodrug thereof, for inducing apoptosis in a neoplastic or cancer cell. In a further aspect, the invention provides use of a continuous intravenous infusion dosage of the compound of Formula I, or a pharmaceutically acceptable prodrug thereof, for the treatment of neoplasia in a mammal. In another aspect, the invention provides use of the compound of Formula I, or a pharmaceutically acceptable prodrug thereof, in the preparation of a continuous intravenous infusion medicament for the treatment of neoplasia in a mammal. In one embodiment, the pharmaceutical composition for treating neoplasia comprises the compound of Formula I and at least one further therapeutic agent selected from the group consisting of chemotherapeutic agents, biological response modifiers, multidrug reversing agents and target specific antitumor agents. In a further aspect, this invention provides a commercial package, kit or system for continuous intravenous infusion, comprising a continuous intravenous infusion dosage of the compound of Formula I, or a pharmaceutically acceptable salt or prodrug thereof, together with instructions for use in the treatment of neoplasia in a mammal. In one embodiment, the infusion dosage is a concentrated form and the commercial package, kit or system further comprises a pre-filled syringe or other container containing an aqueous media for reconstitution of the infusion dosage. In another embodiment, the commercial package, kit or system further comprises an infusion bag. In another embodiment, the commercial package, kit or system further comprises connectors. In yet another embodiment, the commercial package, kit or system further comprises an administration set including a pump connector and anti-siphon valve. In another embodiment, the commercial package, kit or system further comprises an ambulatory infusion pump.

In one embodiment, the cancer cell, neoplasm or pre-cancerous or cancerous condition, in the above-mentioned methods and uses, is selected from leukemia, melanoma, breast cancer, lung cancer, pancreatic cancer, ovarian cancer, renal cancer, colon or colorectal cancer, prostate cancer, and CNS cancer. In another embodiment, the cancer cell, and pre-cancerous or cancerous condition, in the above-mentioned methods and uses, is selected from leukemia, breast cancer, prostate cancer, and CNS cancer.

In another embodiment, in any of the above-mentioned methods and uses, the compound of Formula I for continuous intravenous infusion is formulated to be administered over a period of at least 8 hours per day, at a dosage of about 0.5 to about 150 mg/kg per day over a period of about 1 day to about 28 days. Preferably, the dosage is about 0.5 to about 100 mg/kg per day, or about 1.0 to about 50 mg/kg per day. Preferably, the continuous intravenous infusion is administered 24 hours per day, over a period of about 7 days to about 14 days. Most preferably, the dosage is about 30 to 500 mg/m$^2$ of body surface area, per day.

DETAILED DESCRIPTION OF THE INVENTION

Figure 1:
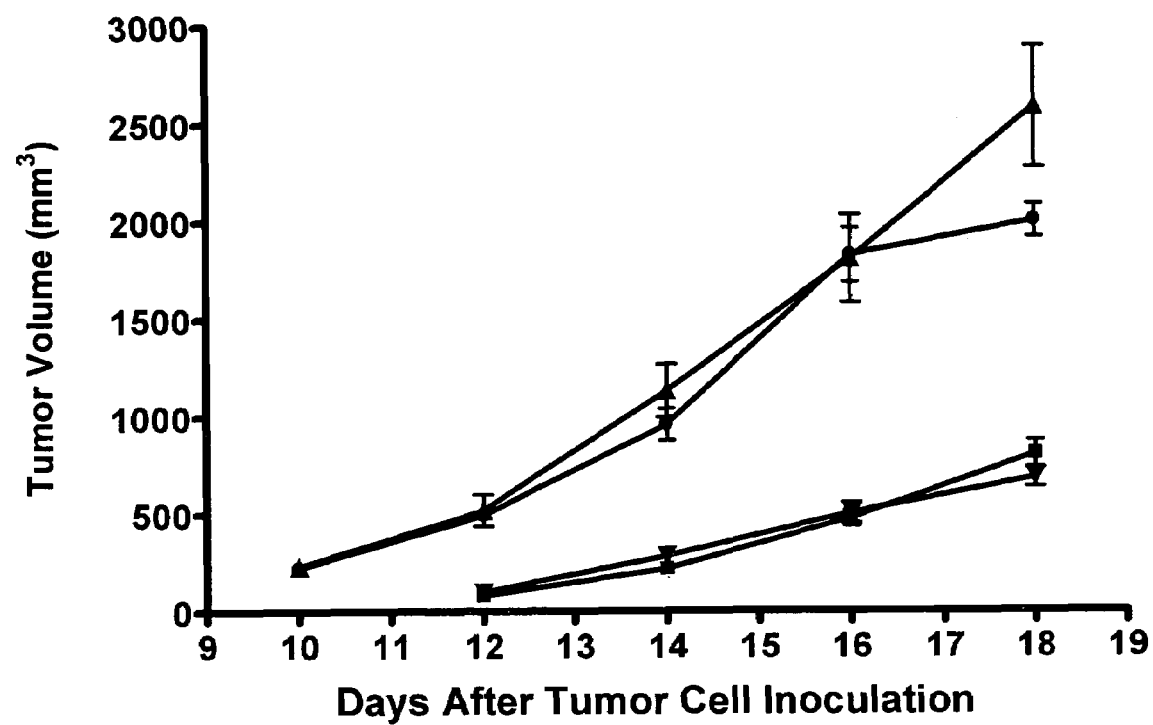
FIG. 1: shows in vivo antitumor activity of Formula I against the rat glioma (C6) tumor xenograft in female athymic (nu/nu) nude mice when given IP at 20 mg/kg (days 6-13) followed by 10 mg/kg (days 14-18) (upside down triangle), SC at 30 mg/kg (days 6-13) followed by 15 mg/kg (days 14-18) (square), and IV at 100 mg/kg (days 6-10 and days 13-17) (triangle), compared to the vehicle control group (circle) given IP at 5 mL/kg (days 6-18). Treatment was initiated when tumors were palpable (day 6).

The present invention also provides methods for treating a neoplastic disorder in a mammal. The methods comprise administering a therapeutically effective amount of the compound of Formula I by continuous intravenous infusion, or pharmaceutically acceptable prodrug thereof to a mammal in need of treatment.

The present invention also provides pharmaceutical compositions comprising the compound of Formula I for use in continuous intravenous infusion and its pharmaceutically acceptable prodrugs.

I. Farnesylated Dibenzodiazepinone Compound

In one aspect, the invention relates to a farnesyl dibenzodiazepinone having the chemical structure represented by Formula I below:

Formula I

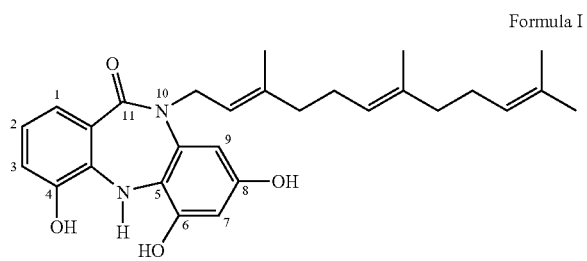

The "compound of Formula I" or simply "Formula I", "active ingredient" or "drug", or equivalent expressions used herein, may be described as a dibenzodiazepinone having a farnesyl substituent located on the nitrogen atom in the 10 position of the dibenzodiazepine ring (i.e., the amide nitrogen in the diazepinone ring), and three phenolic hydroxy substituents in the 4, 6 and 8 positions of the dibenzodiazepinone ring, namely 10-farnesyl-4,6,8-trihydroxy-dibenzodiazepin-11-one. The term also includes pharmaceutically acceptable prodrugs thereof.

The term "pharmaceutically acceptable prodrug" means any pharmaceutically acceptable ester, salt of an ester or any other derivative of a farnesyl dibenzodiazepinone, which upon administration to a mammal is capable of providing, either directly or indirectly, a compound of formula I or a biologically active metabolite or residue thereof. Particularly favored salts or prodrugs are those with improved properties, such as solubility, efficacy, or bioavailability of the compounds of this invention when such compounds are administered to the mammal (e.g., by allowing an orally administered compound to be more readily absorbed into the blood) or which enhance delivery of the parent compound to a biological compartment (e.g., the brain or lymphatic system) relative to the parent species. Exemplary prodrugs of the compound of Formula I include compounds wherein one or more of the 4, 6 and 8-hydroxy groups is bounded to any group that, when administered to a mammalian subject, is cleaved to form the free hydroxyl group. Examples of prodrugs include, but are not limited to, acetate, formate, hemisuccinate, benzoate, dimethylaminoacetate and phosphoryloxycarbonyl derivatives of hydroxy functional groups; dimethylglycine esters, aminoalkylbenzyl esters, aminoalkyl esters or carboxyalkyl esters of hydroxy functional groups. Carbamate and carbonate derivatives of the hydroxy groups are also included. Derivatizations of hydroxyl groups also encompassed, are (acyloxy)methyl and (acyloxy)ethyl ethers, wherein the acyl group is an alkyl group optionally substituted with groups including, but not limited to, ether, amino and carboxylic acid functionalities, or where the acyl group is an amino acid ester. Also included are phosphate and phosphonate esters, sulfate esters, sulfonate esters, which are in alkylated (such as bis-pivaloyloxymethyl (POM) phosphate triester) or in the salt form (such as sodium phosphate ester ($-P(O)O^-_2Na^+_2$)). For further examples of prodrugs used in anticancer therapy and their metabolism, see Rooseboom et al (2004), *Phamacol Rev*, vol 56, 53-102. When the prodrug contains an acidic or basic moiety, the prodrug may also be prepared as its pharmaceutically acceptable salt.

As used herein, abbreviations have their common meaning. Unless otherwise noted, the abbreviations "IP", "IV", "SC", "PO", "CIV", "SEM" and "SD", respectively refer to intraperitoneal, intravenous, subcutaneous, oral (per os), continuous intravenous, standard error of the mean, and standard deviation. Abbreviations in the specification correspond to units of measure, techniques, properties or compounds as follows: "min" means minutes, "h" means hour(s), "D" means day(s), "µL" means microliter(s), "mL" means milliliter(s), "mg" means milligram(s), "g" means gram(s), "mM" means millimolar and "µM" means micromolar.

II. Pharmaceutical Compositions Comprising a Farnesyl Dibenzodiazepinone

The farnesyl dibenzodiazepinone may be formulated into a pharmaceutical composition comprising a compound of Formula I in combination with a pharmaceutically acceptable carrier. The pharmaceutical composition comprising the farnesyl dibenzodiazepinone is useful for treating diseases and disorders associated with uncontrolled cellular growth and proliferation, such as a neoplastic condition. The pharmaceutical composition comprising the farnesyl dibenzodiazepinone may be packaged into a convenient commercial package providing the necessary materials, such as the pharmaceutical composition and written instructions for its use in treating a neoplastic condition, in a suitable container.

The compounds of the present invention, or pharmaceutically acceptable prodrugs thereof, are formulated for continuous intravenous (CIV) infusion administration for the therapeutic or prophylactic treatment of neoplastic and proliferative diseases and disorders. Any known device useful for infusion of drug formulations can be used to effect such administration. For administration, the compound can be mixed with conventional pharmaceutical carriers and excipients and used in the form of a solution. The administrable compositions comprising a compound of the present invention will contain from about 0.01% to about 30%, about 0.05% to about 25%, about 0.05% to about 15%, about 0.1% to about 10% or about 0.1% to about 5% by weight of the active compound.

The pharmaceutical preparations disclosed herein are prepared in accordance with standard procedures and are administered at dosages that are selected to reduce, prevent, or eliminate cancer. (See, e.g., Gennaro A R (ed), *Remington's Pharmaceutical Sciences*, 2000, Mack Publishing Company, Easton, Pa.; and Goodman and Gilman, *Pharmaceutical Basis of Therapeutics*, 2001, Pergamon Press, New York, N.Y., the contents of which are incorporated herein by reference, for a general description of the methods for administering various agents for human therapy).

As used herein, the term "unit dosage" refers to physically discrete units suitable as unitary dosages for human subjects and other mammals, each unit containing a predetermined quantity of farnesyl dibenzodiazepinone calculated to produce the desired therapeutic effect, in association with a suitable pharmaceutically acceptable carriers. In one embodiment, the unit dosage contains from about 10 to about 1000 mg of active ingredient, per $m^2$ of body surface of the subject, per day. In another embodiment, the unit dosage contains from about 20 to about 750 mg of active ingredient, per $m^2$ of body surface of the subject, per day. In another embodiment, the unit dosage contains from about 30 to about 500 mg of active ingredient, per $m^2$ of body surface of the subject, per day. The unit dosage may be compounded for several days, for example, for the administration of a dose of 30 mg/$m^2$/day over a 7-day period, the unit dosage includes at least 378 mg of active ingredient, for a human subject of 1.8 $m^2$ of body surface area. The unit dosage for a 7-day infusion may contain from about 300 mg to 10 000 mg of active ingredient.

The pharmaceutically acceptable compositions of the present invention comprise the compound of the present invention in association with one or more non-toxic, pharmaceutically acceptable carriers and/or diluents and/or adjuvants and/or excipients, collectively referred to herein as "carrier" materials, and if desired other active ingredients. Pharmaceutically acceptable carriers include, for example, solvents, vehicles or medium such as saline, buffered saline, dextrose, water, glycerol, ethanol, propylene glycol, polysorbate 80 (e.g., Tween-80™ or Crillet 4 HP™), poly(ethylene glycol) 300 and 400 (PEG 300 and 400), PEGylated castor oil (E.g. Cremophor EL), poloxamer 407 and 188, hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The term specifically excludes cell culture medium.

Excipients or additives included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, antibacterials, chelating agents, administration aids, and combinations thereof. The compositions may contain common carriers and excipients, such as, but not limited to, sodium citrate, citric acid, sodium chloride, mannitol, glucose, ascorbic acid, sodium ascorbate.

Formulations for CIV administration can be in the form of aqueous or non-aqueous isotonic sterile injection solutions, suspensions or fat emulsions, comprising a compound of this invention, or a pharmaceutically acceptable prodrug thereof. The CIV form used for injection must be fluid to the extent that easy syringability exists. These solutions or suspensions can be prepared from sterile concentrated liquids, powders or granules. The compounds can be dissolved in a carrier such as a solvent or vehicle, for example, polyethylene glycol, propylene glycol, ethanol, corn oil, benzyl alcohol, glycofurol, N,N-dimethylacetamide, N-methylpyrrolidone, glycerine, saline, dextrose, water, glycerol, hydrophobic carriers, and combinations thereof.

Excipients used in CIV preparations also include, without limitation, stabilizing agents (e.g. carbohydrates, amino acids and polysorbates), solubilizing agents (e.g. cetrimide, sodium docusate, glyceryl monooleate, polyvinylpyrolidone (PVP) and polyethylene glycol (PEG)) and surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

CIV formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of the compound can be a ready-to-use solution of the compound or a salt thereof in a suitable carrier in sterile, hermetically sealed ampoules or in sterile pre-loaded syringes, or containers suitable for use with an infusion pump, e.g. infusion bags. The suitable carrier optionally comprises any of the above-mentioned excipients.

Alternatively, the unit dosage for of the compound of the present invention can be in a concentrated liquid, powder or granular form for ex tempore reconstitution in the appropriate pharmaceutically acceptable carrier at the time of delivery. In addition the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

For example, a sterile formulation of the compound of Formula I and optionally one or more additives, including solubilizers or surfactants, can be dissolved or suspended in any of the commonly used intravenous fluids and administered by infusion. Intravenous fluids include, without limitation, physiological saline, phosphate buffered saline, 5% glucose or dextrose or Ringer=s™ solution.

III. Methods for Treating Neoplasms

In one aspect, the invention relates to a method for inhibiting growth and/or proliferation of cancer cells in a mammal. In another aspect, the invention provides a method for treating neoplasms in a mammal. Mammals include ungulates (e.g. sheeps, goats, cows, horses, pigs), and non-ungulates, including rodents, felines, canines and primates (i.e. human and non-human primates). In a preferred embodiment, the mammal is a human.

As used herein, the terms "neoplasm", "neoplastic disorder", "neoplasia" "cancer," "tumor" and "proliferative disorder" refer to cells having the capacity for autonomous growth, i.e., an abnormal state of condition characterized by rapidly proliferating cell growth which generally forms a distinct mass that show partial or total lack of structural organization and functional coordination with normal tissue. The terms are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the invention include leukemia, and hepatocellular cancers, sarcoma, vascular endothelial cancers, breast cancers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer.

The farnesyl dibenzodiazepinone is brought into contact with or introduced into a cancerous cell or tissue. In general, the methods of the invention for delivering the compositions of the invention in vivo utilize art-recognized protocols for delivering therapeutic agents with the only substantial procedural modification being the substitution of the farnesyl dibenzodiazepinone of the present invention for the therapeutic agent in the art-recognized protocols. The route by which the farnesyl dibenzodiazepinone is administered, as well as the formulation, carrier or vehicle will depend on the location as well as the type of the neoplasm. A wide variety of administration routes can be employed. The farnesyl dibenzodiazepinone may be administered by intravenous or intraperitoneal infusion or injection. For example, for a solid neoplasm that is accessible, the farnesyl dibenzodiazepinone may be administered by injection directly into the neoplasm. For a hematopoietic neoplasm the farnesyl dibenzodiazepinone may be administered intravenously or intravascularly. For neoplasms that are not easily accessible within the body, such as metastases or brain tumors, the farnesyl dibenzodiazepinone may be administered in a manner such that it can be transported systemically through the body of the mammal and thereby reach the neoplasm and distant metastases for example intrathecally, intravenously, intraventricularly, intramuscularly or orally. The farnesyl dibenzodiazepinone can also be administered subcutaneously, intraperitoneally, topically (for example for melanoma), rectally (for example colorectal neoplasm) vaginally (for example for cervical or vaginal neoplasm), nasally or by inhalation spray (for example for lung neoplasm). A continuous infusion may also be given intraventricularly, intraarterially (e.g. infusion through hepatic artery for liver cancer), intracavitary (e.g. intraperitoneal for ovarian cancer), or intravesically (e.g. to treat bladder cancer). The preferred route of administration of the present invention is by continuous intravenous infusion.

The farnesyl dibenzodiazepinone is administered in an amount that is sufficient to inhibit the growth or proliferation of a neoplastic cell, or to treat a neoplastic disorder. The term "inhibition" refers to suppression, killing, stasis, or destruction of cancer cells. The inhibition of mammalian cancer cell growth according to this method can be monitored in several ways. Cancer cells grown in vitro can be treated with the compound and monitored for growth or death relative to the same cells cultured in the absence of the compound. A cessation of growth or a slowing of the growth rate (i.e., the doubling rate), e.g., by 50% or more at 100 micromolar, is indicative of cancer cell inhibition (see Anticancer Drug Development Guide: preclinical screening, clinical trials and approval; B. A. Teicher and P. A. Andrews, ed., 2004, Humana Press, Totowa, N.J.). Alternatively, cancer cell inhibition can be monitored by administering the compound to an animal model of the cancer of interest. Examples of experimental non-human animal cancer models are known in the art and described below and in the examples herein. A cessation of tumor growth (i.e., no further increase in size) or a reduction in tumor size (i.e., tumor volume by least a 58%) in animals treated with the compound relative to tumors in control animals not treated with the compound is indicative of significant tumor growth inhibition (see Anticancer Drug Development Guide: preclinical screening, clinical trials and approval; B. A. Teicher and P. A. Andrews, ed., 2004, Humana Press, Totowa, N.J.).

The term "treatment" refers to the application or administration of a farnesyl dibenzodiazepinone to a mammal, or application or administration of a farnesyl dibenzodiazepinone to an isolated tissue or cell line from a mammal, who has a neoplastic disorder, a symptom of a neoplastic disorder or a predisposition toward a neoplastic disorder, with the purpose to cure, heal, alleviate, relieve, alter, ameliorate, improve, or control the disorder, the symptoms of disorder, or the predisposition toward disorder. The term "treating" is defined as administering, to a mammal, an amount of a farnesyl dibenzodiazepinone sufficient to result in the prevention, reduction or elimination of neoplastic cells in a mammal ("therapeutically effective amount"). The therapeutically effective amount and timing of dosage will be determined on an individual basis and may be based, at least in part, on consideration such as the age, body weight, sex, diet and general health of the recipient subject, on the nature and severity of the disease condition, and on previous treatments and other diseases present. Other factors also include the duration of administration, drug combination, the tolerance of the recipient subject to the compound and the type of neoplasm or proliferative disorder. In one embodiment, a therapeutically effective amount of the compound is in the range of about 0.5 to about 150 mg/kg of body weight of the mammal per day, about 0.5 to about 100 mg/kg body weight per day, or about 1 to about 50 mg/kg body weight per day. The therapeutically effective doses of the above embodiments may also be expressed in milligrams per square meter ($mg/m^2$), e.g. in the case of a human patient. In another embodiment, a therapeutically effective amount of the compound is in the range of about 10 mg to about 1000 mg of active ingredient per $m^2$ of body surface of the subject, per day, from about 20 mg to about 750 mg of active ingredient per $m^2$ of body surface of the subject, per day, from about 30 mg to about 500 mg of active ingredient, per $m^2$ of body surface of the subject, per day, or from about 120 mg to about 480 mg of active ingredient, per $m^2$ of body surface of the subject, per day. Conversion factors for different mammalian species may be found in Freireich et al, Quantitative comparison of toxicity of anti-cancer agents in mouse, rat, dog, monkey and man, *Cancer Chemoth. Report*, 1966, 50(4): 219-244).

To monitor the efficacy of tumor treatment in a human subject, tumor size and/or tumor morphology is measured before and after initiation of the treatment, and treatment is considered effective if either the tumor size ceases further growth, or if the tumor is reduced in size, e.g., by at least 10% or more (e.g., 20%, 30%, 40%, 50%, 60%, 70%, 80%, 90% or even 100%, that is, the absence of the tumor). Prolongation of survival, time-to-disease progression, partial response and objective response rate are surrogate measures of clinical activity of the investigational agent. Tumor shrinkage is considered to be one treatment-specific response. This system is limited by the requirement that patients have visceral masses that are amenable to accurate measurement. Methods of determining the size of a tumor in vivo vary with the type of tumor, and include, for example, various imaging techniques well known to those in the medical imaging or oncology fields (MRI, CAT, PET, etc.), as well as histological techniques and flow cytometry. For certain types of cancer, evaluation of serum tumor markers are also used to evaluate response (eg prostate-specific antigen (PSA) for prostate cancer, and carcino-embryonic antigen (CEA), for colon cancer). Other methods of monitoring cancer growth include cell counts (e.g. in leukemias) in blood or relief in bone pain (e.g. prostate cancer).

The dosage unit is compounded for delivery over several days, e.g., using, an intravenous infusion of the farnesyl dibenzodiazepinone compound over a several day period. In this embodiment, the dosage unit contains a corresponding multiple of the daily dose. The effective dose is administered as an infusion, e.g. over a period of about 8 hours to about 24 hours per day. The compound may be administered as a treatment, for up to 30 days. Preferably, the effective dose is administered as a continuous intravenous (CIV) infusion over 24 hours, for a period of about 1 to about 30 days, preferably for a period of about 7 to about 14 days. Moreover, treatment of a subject with a therapeutically effective amount of a composition can include a single treatment or a series of treatments. For example, the treatment can be administered as a 24 hours CIV infusion, for a duration of 28 days, repeated four times, with a resting period between each treatment. Another example includes 14-day treatments separated by 7-day resting periods. Estimates of effective dosages, toxicities and in vivo half-lives for the farnesyl dibenzodiazepinone compound can be made using conventional methodologies or on the basis of in vivo testing using an appropriate animal model.

The farnesyl dibenzodiazepinone may be administered in conjunction with or in addition to known anticancer compounds or chemotherapeutic agents. Such agents include, but are not limited to, 5-flurouracil, mitomycin C, methotrexate, hydroxyurea, nitrosoureas (e.g., BCNU, CCNU), cyclophosphamide, dacarbazine, thiotepa, atreptozocine, temozolomide, enzastaurin, erlotinib, mitoxantrone, anthracyclins (Epirubicin and Doxurubicin), etoposide, pregnasome, platinum compounds such as carboplatin and cisplatin, taxanes such as paclitaxel and docetaxel; hormone therapies such as tamoxifen and anti-estrogens; antibodies to receptors, such as herceptin and Iressa; aromatase inhibitors, progestational agents and LHRH analogs; biological response modifiers such as IL2 and interferons; multidrug reversing agents such as the cyclosporin analog PSC 833.

Toxicity and therapeutic efficacy of farnesyl dibenzodiazepinone compounds can be determined by standard pharmaceutical procedures in cell cultures or experimental animals. Therapeutic efficacy is determined in animal models as described above and in the examples herein. Toxicity studies are done to determine the lethal dose for 10% of tested animals (LD10). Animals are treated at the maximum tolerated dose (MTD): the highest dose not producing mortality or greater than 20% body weight loss. The effective dose (ED) is related to the MTD in a given tumor model to determine the therapeutic index of the compound. A therapeutic index (MTD/ED) close to 1.0 has been found to be acceptable for some chemotherapeutic drugs, a preferred therapeutic index for classical chemotherapeutic drugs is 1.25 or higher.

The data obtained from cell culture assays and animal studies can be used in formulating a range of dosage for use in humans. The dosage of compositions of the invention will generally be within a range of circulating concentrations that include the MTD. The dosage may vary within this range depending upon the dosage form employed and the schedule of administration utilized. For any compound used in the method of the invention, the therapeutically effective dose can be estimated initially from cell culture assays. A dose may be formulated in animal models to achieve a circulating plasma concentration range of the compound. Such information can be used to more accurately determine useful doses in humans. Levels in plasma may be measured, for example, by high performance liquid chromatography.

Animal models to determine antitumor efficacy of a compound are generally carried out in mice. Either murine tumor cells are inoculated subcutaneously into the hind flank of mice from the same species (syngeneic models) or human tumor cells are inoculated subcutaneously into the hind flank of severe combined immune deficient (SCID) mice or other immune deficient mouse (nude mice) (xenograft models).

Advances in mouse genetics have generated a number of mouse models for the study of various human diseases including cancer. The MMHCC (Mouse models of Human Cancer Consortium) web page (www.cancer.gov), sponsored by the National Cancer Institute, provides disease-site-specific compendium of known cancer models, and has links to the searchable Cancer Models Database (www.cancer.gov), as well as the NCI-MMHCC mouse repository. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of farnesyl dibenzodiazepinone compounds, as well as for determining a therapeutically effective dose.

Unless otherwise indicated, all numbers expressing quantities of ingredients, properties, conditions, activities, pharmacokinetic parameters and so forth used in the specification and claims are to be understood as being modified in all instances by the term "about." Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Example 1

Production and Identification of the Compound of Formula I

The compound of Formula I was isolated from the fermentation broth of either strains of Micromonospora [S01]046 or 046-ECO11 respectively having IDAC 231203-01 and 070303-01 accession numbers (International Depository Authority of Canada (IDAC), Bureau of Microbiology, Health Canada, 1015 Arlington Street, Winnipeg, Manitoba, Canada, R3E 3R2). The compound of Formula I was produced and isolated as described in WO 2004/065591 in August 2004. The structure of the compound of Formula I was identified as described in Canadian Patent application no. 2,507,567.

Example 2

In Vivo Efficacy in C6 Glioma Models

1. In Vivo Efficacy in a C-6 Glioblastoma Model:

The rat C6 glioblastoma antitumor efficacy study was performed at INSERM U318 (Grenoble, France). The rat C6 glioblastoma subcutaneous tumor model is based on the use of a rat C6 cell line obtained from a rat glial tumor induced by N-nitrosomethylurea (Benda et al. (1968), *Science*, vol 161, 370-371). These animal studies were done according to ethical guidelines of animal experimentation (Charte du comité d'éthique du CNRS, 2003) and the English "*Guidelines for the welfare of animals in experimental neoplasia* (Second Edition)" from the *United Kingdom Coordinating Committee on Cancer Research* (*UKCCCR*) (Workman et al. (1998), Br. J. Cancer, vol 77, no 1, 1-10). On each dosing day, Formula I stock solutions (24 and 40 mg/mL in 20% ethanol, 20% PEG-400 and 60% Tween 80) were diluted with sterile 5% dextrose in water (D5W) to prepare dosing solutions of 6 mg/mL and 10 mg/mL of Formula I in a vehicle consisting of 5% ethanol, 5% PEG-400, 15% Tween-80, and 75% D5W.

For the rat glioma antitumor efficacy study, female athymic (nu/nu) nude mice (6-7 weeks of age) were inoculated SC with $5 \times 10^6$ C6 cells (day 0). Tumor bearing animals were randomized (10 per group) when tumors were palpable (day 6). Group 1 (control group) received drug-free vehicle (5% ethanol, 5% PEG-400, 15% Tween-80, and 75% D5W) IP (5 mL/kg), once daily on days 6-18 (q1d×13). Group 2 received Formula I (6 mg/mL) IP at 20 mg/kg, once daily on days 6 to 13 and then at 10 mg/kg once daily on days 14 to 18. Group 3 received Formula I (6 mg/mL) SC at 30 mg/kg, once daily on days 6 to 13 and then at 15 mg/kg once daily on days 14 to 18. Group 4 received Formula I (10 mg/mL) IV at 100 mg/kg q1d×5 for 2 weeks. Each animal was euthanized when its tumor reached the predetermined endpoint size (~2,500 mm$^3$) or at the end of the study (D18). Treatment period was over 13 days, from day 6 to day 18, post tumor cell inoculation. Tumor growth inhibition (TGI) was calculated on day 16 post tumor cell inoculation, at which time some animals from the vehicle control group had to be sacrificed due to tumor burden.

Determination of Antitumor Activity:

In this model and the models of Examples 3, 6 and 7, tumor growth was followed every other day by measuring tumor length (L) and width (W) using a calliper. Measurements were converted to tumor volumes (TV; mm$^3$) using the standard formula, TV=(L×W$^2$)/2. Tumor volume at day n was expressed as relative tumor volume (RTV) according to the following formula RTV=TV$_n$/TV$_0$, where TV$_n$ is the tumor volume at day n and TV$_0$ is the tumor volume at day 0. The percentage of tumor growth inhibition (% TGI) was determined by 1−(mean RTV of treated group/mean RTV of control group)×100. According to the NCI standards, a % TGI of ≧58% (T/C≦42%) is indicative of antitumor activity. Statistical analysis was calculated by the two-tailed unpaired t test using the Prism software. Animals were weighed at least twice weekly during and after treatment until completion of the study. The mice were examined frequently for overt signs of any adverse drug-related side effects. Animals were euthanized if they showed more than 15% body weight loss for 3 consecutive days or 20% body weight loss during a single day.

When the time to endpoint (TTE) for each mouse was also calculated by the following equation:

$$TTE = \frac{\log 10(\text{endpoint volume}) - b}{m}$$

Where TTE is expressed in days, endpoint volume is in mm$^3$, b is the intercept, and m is the slope of the line obtained by linear regression of a log-transformed tumor data set. This value was used to determined % tumor growth delay (% TGD), defined as the increase in median TTE for a treatment group compared to the control group expressed in days, or as a percentage of the median TTE of the control group.

Results:

The compound of Formula I was administered following three different routes, SC, IP or IV, at different concentrations depending on the route of administration. Maximum body weight loss of 15% was observed on Day 13 for the IP group receiving 20 mg/kg (Q1D×8) followed by 10 mg/kg (Q1D×7) and 11% for the SC group receiving 30 mg/kg (Q1D×8) followed by 15 mg/kg (Q1D×7). No significant body weight loss was observed for the IV group. The effect of the different treatment routes on tumor growth inhibition was analyzed at Day 18. The efficacy data (FIG. 1) showed that daily bolus administrations of Formula I either IP or SC resulted in significant antitumor efficacy in this tumor model, resulting in % TGI of 66% and 60% (P<0.0001). No significant difference in tumor volume relative to the vehicle control was noted for intravenous (IV) bolus administration of Formula I at 100 mg/kg (Q1D×5) over 2 weeks.

2. Efficacy of Formula I Against Orthotopic C6 Glioma Xenograft

The antitumor activity of the compound of formula I was further tested in a orthotopic C6 glioma tumor xenograft model in mice. CD1 female nude mice (6 weeks of age) were grafted intra-cerebrally with $5 \times 10^4$ (volume of 10 microliters) rat C6 glioma cells (day 0). Treatment was initiated 24 h after tumor cell implantation. The compound of Formula I was administered intraperitoneally (IP) at a concentration of 30 mg/kg (volume of 10 mL/Kg) on days 1, 2 and 3 followed by IP injections of 10 mg/kg on days 4 and 5 and 9 to 38. Vehicle (30% PEG; 30% PG; 40% H$_2$O) was injected in a volume of 10 mL/kg using the same route and schedule.

Body weight of animals was monitored every other day and the effect of the compound of Formula I on growth of intracerebral glioma tumors was evaluated by mouse survival and percentage increase in life span (% ILS, expressed as mean survival time of treated animals minus the mean survival time of the control group). By criteria established by the National Cancer Institute, increases in life span exceeding 25% indicate that the drug has significant antitumor activity (Plowman et al. (1997) Human tumor xenografts models in NCI drug development. In: Theicher B A (ed) Anticancer drug development guide: prescreening, clinical trials and approval. Human press, Totowa, pp 101-125). Statistical analysis of mouse survival was performed by Kaplan-Mayer analysis.

Figure 2:
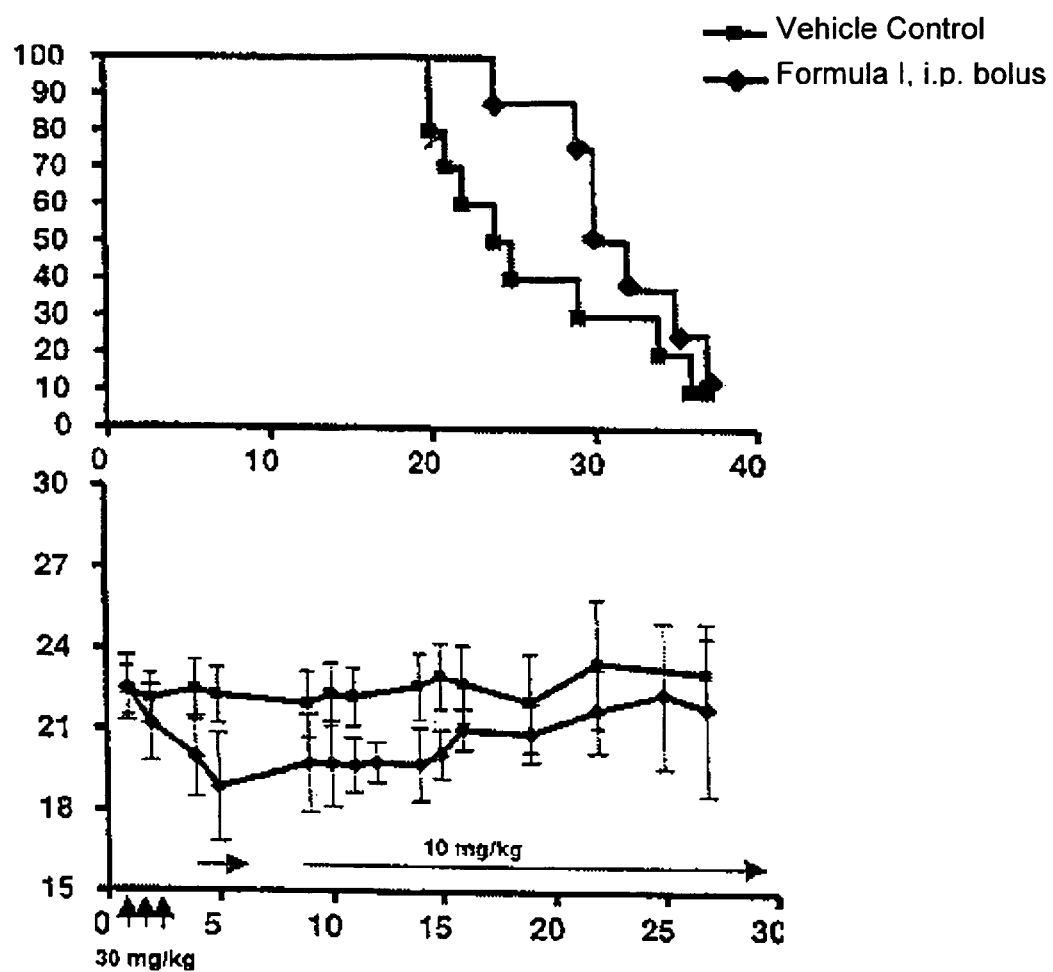
FIG. 2: shows the survival of mice xenografted with orthotopic C6 glioma tumor, treated daily with vehicle (squares) or the compound of Formula I (circles). Daily treatment with the compound of Formula I led to an increase survival of 7 days resulting in a 29% increase in life span.

Daily treatment with the compound of Formula I led to an increase survival of 7 days resulting in a 29% increase in life span (see FIG. 2).

Example 3

In Vivo Antitumor Efficacy in a U-87MG Glioma Model

The human U-87 MG (ATCC® no. HTB-14™) glioblastoma antitumor efficacy study was performed at INSERM U318 (Grenoble, France). The U-87MG cell line is derived from a brain glioblastoma of a 44-year-old Caucasian female. These animal studies were done according to ethical guidelines of animal experimentation (Charte du comité d'éthique du CNRS, 2003) and the English guidelines of for the welfare of animals in experimental neoplasia (Workman et al., 1998, supra). On each dosing day, Formula I stock solutions (24 and 40 mg/mL in 20% ethanol, 20% PEG400 and 60% Tween 80) were diluted with sterile 5% dextrose in water (D5W) to prepare a dosing solution of 6 mg/mL of the compound of Formula I in a vehicle consisting of 5% ethanol, 5% PEG-400, 15% Tween-80, and 75% D5W.

For the human glioblastoma antitumor efficacy study, female athymic (nu/nu) nude mice (6-7 weeks of age) were inoculated SC with $5\times10^6$ U-87MG cells (day 0). Tumor bearing animals were randomized (10 per group) when tumors were palpable (day 24). Group 1 (control group) received drug-free vehicle (5% ethanol, 5% PEG-400, 15% Tween-80, and 75% D5W) SC (5 mL/kg), once daily q1d×15. Group 2 received Formula I (6 mg/mL) SC at 30 mg/kg, q1d×5 over 2 weeks (days 24-28 and 32-35). Group 3 (positive control group) received temozolomide PO at 150 mg/kg, q4d×3. Each animal was euthanized when its tumor reached the predetermined endpoint size (~2,500 mm$^3$) or at the end of the study (D40). Tumor growth inhibition (TGI) was calculated on day 34 post tumor cell inoculation, at which time some animals from the vehicle control group had to be sacrificed due to tumor burden.

Figure 3:
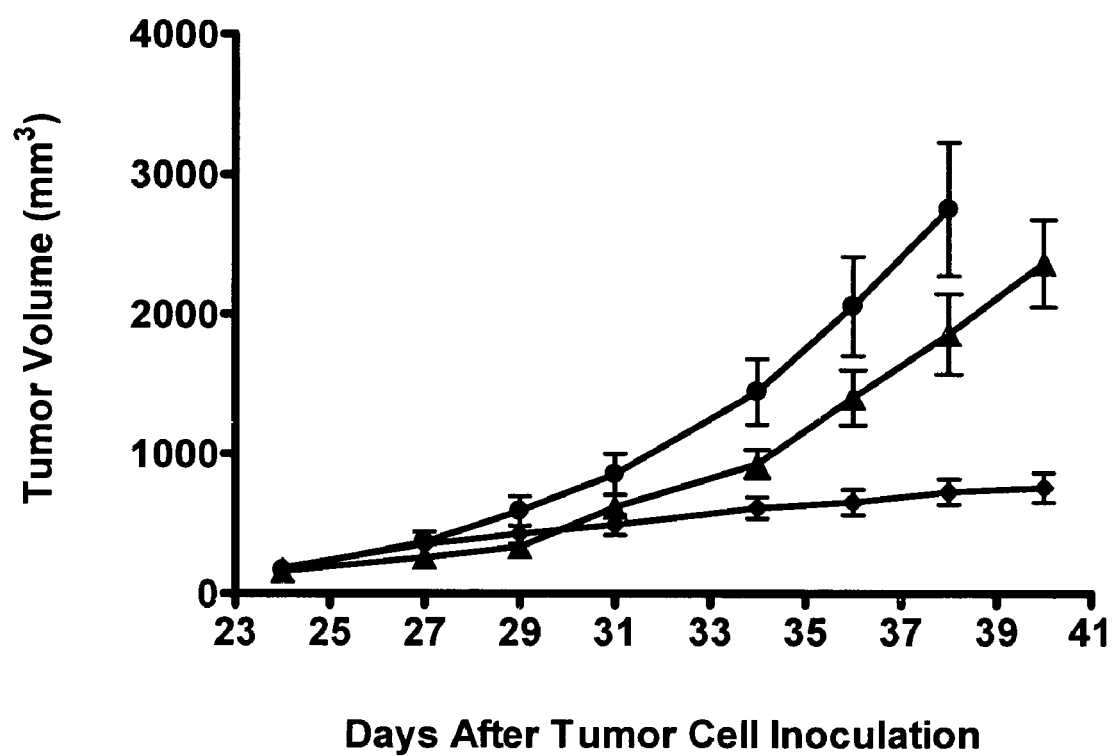
FIG. 3: shows tumor volume growth curves of the different groups (mean±SEM) from in vivo antitumor activity of Formula I against the human glioma (U-87MG) tumor xenograft. Treatment was initiated when tumors were palpable (day 24). Formula 1 (30 mg/kg) (square) and drug-free control vehicle (5 mL/kg) (circle) were given SC once daily (Monday to Friday) for 2 weeks (q1dx5) 2 wk. Temodozolimide (diamond-shaped), used as positive control, was given PO at 150 mg/g every four days (total of 3 treatments).
Figure 4:
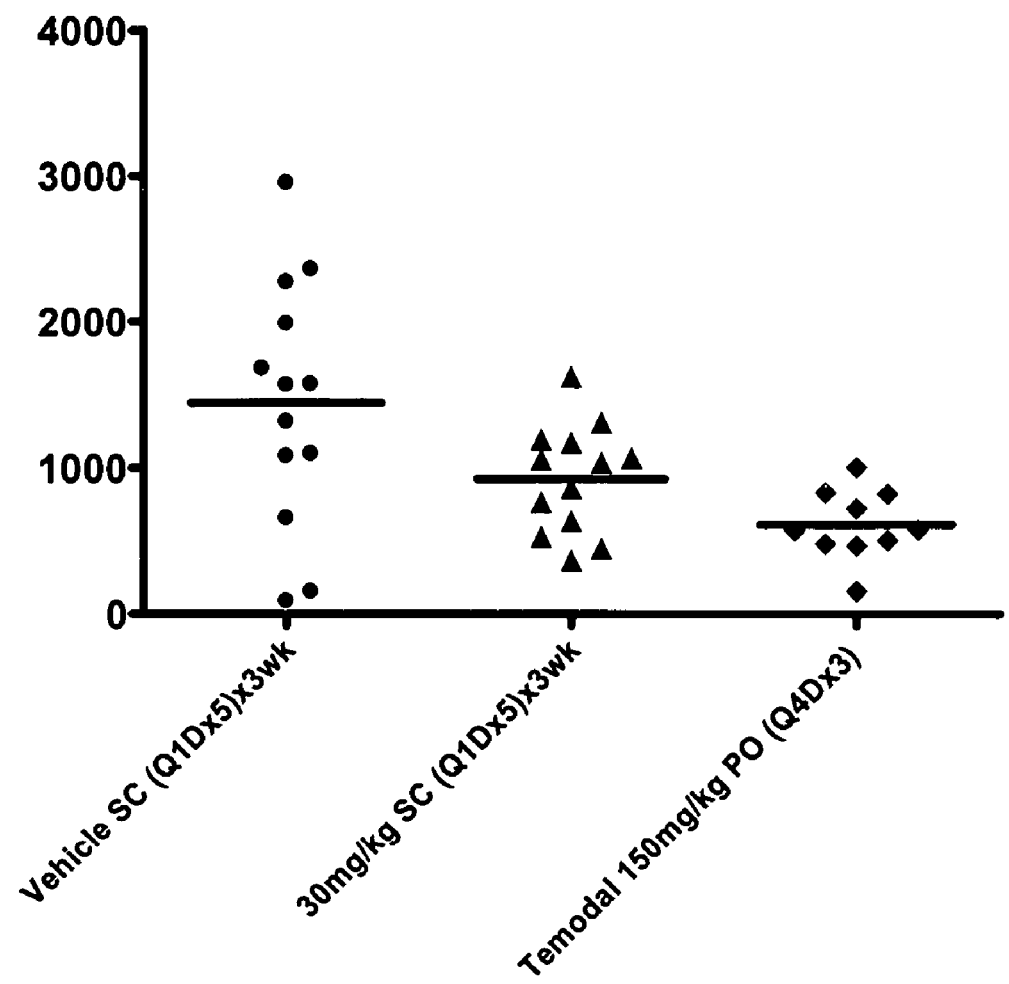
FIG. 4: shows tumor volumes of all the animals from the different treatment groups of the in vivo activity assay of FIG. 3, when compared at day 34, after which time animals from the control group had to be sacrificed due to tumor burden.

Formula I has demonstrated in vitro activity in this cell line with an IC$_{50}$ of 10.9 µM. Formula I antitumor activity in this model was tested by SC bolus injection (FIG. 3). The dose regimen was well tolerated with no significant body weight loss observed throughout the study. TGI was calculated at day 34, time at which some animals from the vehicle control group had to be sacrificed due to tumor burden. Moderate antitumor efficacy (% TGI=36%; P=0.05) was observed when Formula I was administered on a daily basis (FIG. 4).

Example 4

Pharmacokinetics

The compound of formula I was dissolved in ethanol (5%), Polysorbate 80 (15%), PEG 400 (5%) and dextrose (5%) at a final concentration of 6 mg/ml (IV, IP and SC administration). For oral administration, the compound of Formula I was solubilized in Chremophor® EL/Ethanol (50%:50%) at a final concentration of 6 mg/ml. Prior to dosing, animals (female Crl: CD1 mice; 6 weeks of age, 22-24 g) were weighed, randomly selected and assigned to the different treatment groups. The compound of Formula I was administered by the bolus intravenous (IV), bolus subcutaneous (SC), bolus intraperitoneal (IP), or oral (PO) route to the assigned animals. The dosing volume of Formula I was 5 mL per kg body weight. Animals were anesthetized prior to bleeding with 5% isoflurane. Blood was collected into microtainer tubes containing the anticoagulant K$_2$EDTA by cardiac puncture from each of 4 animals per bleeding timepoint (2 min, 5 min, 15 min, 30 min, 1 h, 2 h, 4 h and 8 h). Following collection, the samples were centrifuged and the plasma obtained from each sample was recovered and stored frozen (at approximately −80° C.) pending analysis. At the 5 min and 30 min time points, the following organs were harvested from each animal: brain, lungs, skeletal muscle, fat tissue, kidneys, spleen, thymus and liver. Tissues were frozen (at approximately −80° C.) pending analysis. Samples were analysed by LC/MS/MS. Standard curve ranged from 25 to 2000 ng/mL with limit of quantitation (LOQ)≦25 ng/mL and limit of detection (LOD) of 10 ng/mL.

Plasma values of the compound of Formula I falling below the limit of quantitation (LOQ) were set to zero. Mean concentration values and standard deviation (SD) were calculated at each timepoints of the pharmacokinetic study (n=4 animals/timepoint). The following pharmacokinetic parameters were calculated: area under the plasma concentration versus time curve from time zero to the last measurable concentration time point (AUC0-t), area under the plasma concentration versus time curve extrapolated to infinity (AUCinf), maximum observed plasma concentration (Cmax), time of maximum plasma concentration (tmax), apparent first-order terminal elimination rate constant (kel), apparent first-order terminal elimination half-life will be calculated as 0.693/kel (t$_{1/2}$). The systemic clearance (CL) of the compound of Formula I after intravenous administration was calculated using Dose/AUCinf. Pharmacokinetic parameters were calculated using Kinetica™ 4.1.1 (InnaPhase Corporation, Philadelphia, Pa.).

Results

Figure 5:
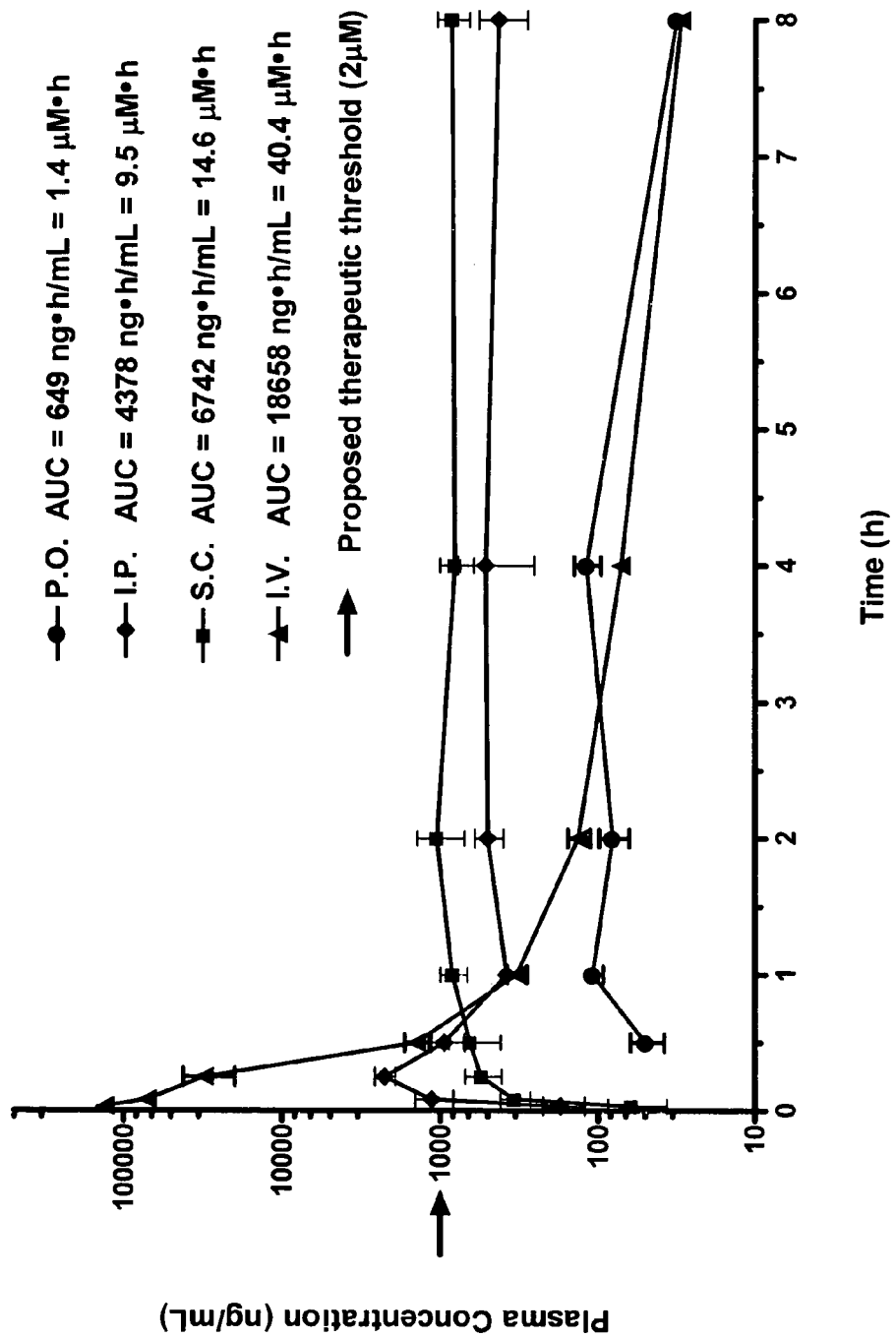
FIG. 5: shows the mean (±SD) plasma concentrations of the compound of Formula I in Swiss mice following 30 mg/kg bolus intravenous (IV), bolus intraperitoneal (IP), subcutaneous (SC) and oral (PO) administrations.

Mean plasma concentrations of the compound of Formula I following bolus intravenous (IV), bolus intraperitoneal (IP), bolus subcutaneous (SC), and oral (PO) administrations at 30 mg/kg are presented in FIG. 5.

Mean (±SD) plasma concentrations of the compound of Formula I following bolus IV administration of a 30 mg/kg dose declined rapidly in a biexponential manner resulting in very short half lives (t$_{1/2}$ α and β of 4.6 min and 2.56 h, respectively). On the other hand, the pharmacokinetics of the compound of Formula I following intraperitoneal and subcutaneous administrations showed a PK profile suggestive of slow release. With both these routes of administration, the compound plasma concentration is sustained and maintained at therapeutically relevant levels for over 8 hours. Oral administration results in moderate but sustained drug levels. These data indicate that the compound of Formula I is orally bioavailable (~5-8% when compared to IV bolus administration).

Figure 6:
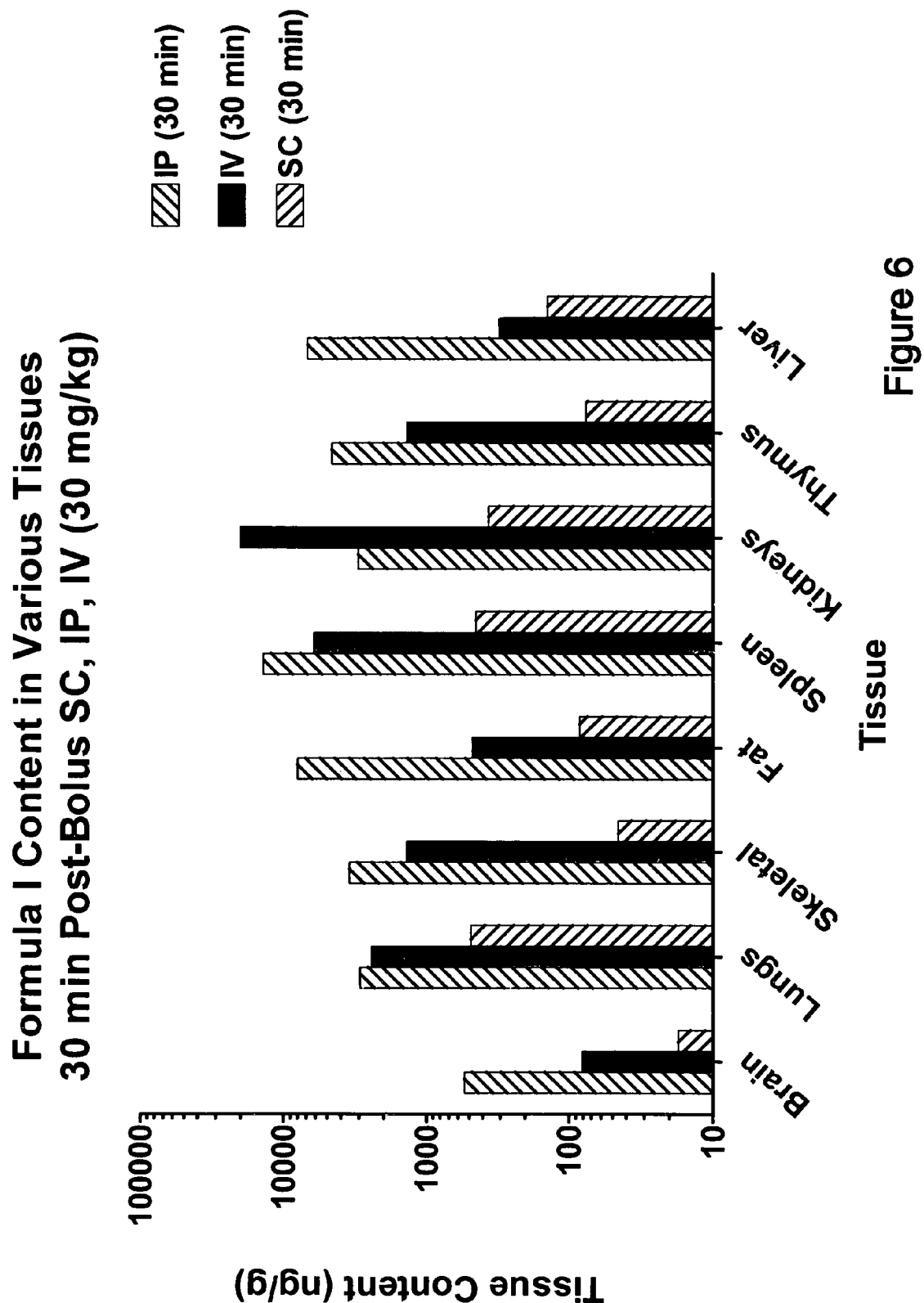
FIG. 6: shows the mean concentration of the compound of Formula I in various tissues, 30 minutes after 30 mg/kg intravenous (IV), intraperitoneal (IP) and subcutaneous (SC) bolus administrations.

Mean tissue concentrations of the compound of Formula I 130 min after bolus intravenous (IV), bolus intraperitoneal (IP) or bolus subcutaneous (SC) administrations at 30 mg/kg are presented in FIG. 6. The 30 min time point was chosen since plasma concentrations were similar with all three routes of administration. Compound of formula I is well distributed following IV and IP bolus dosing. Surprisingly, although IP and SC bolus administrations resulted in a similar PK profile, tissue levels were significantly lower following sc dosing.

This could be explained by the absence of peak levels following SC bolus administration compared with IV and IP bolus administrations.

Example 5

Efficacy of Formula I Against Murine P388 Leukemia Model

The anticancer activity of the compound of Formula I was further tested in a murine P388 leukemia model in mice.

Formulation: The compound of Formula I is first dissolved in 1 volume of 90% propylene glycol (PG). This is followed by the addition of 2 volumes of 45% polyethylene glycol 400 (PEG 400). The volume ratio of PEG 400/PG/water is respectively 30:30:40. Compound is injected in a volume of 10 mL/kg.

DBA/2 female mice (6 weeks of age) were injected intraperitoneally (IP) with $1 \times 10^6$ P388 murine leukemia cells (day 0). Mice were randomized in 4 groups (10 mice per group) at Day 1 and treated with the following dose and schedule:

Group 1: IV injection of vehicle (PEG/PG formulation) on D1 and D8, daily IP administration of vehicle from D2 to D7 and from D9 to D10

Group 2: iv injection of the compound of Formula I in PEG-PG formulation at 50 mg/kg on D1 followed by daily IP administration of the compound of Formula I in PEG-PG formulation at 10 mg/kg from D2 to D4 and from D6 to D12

Group 3: Daily IP administration of the compound of Formula I in PEG-PG formulation at 10 mg/kg from D1 to D4 and from D8 to D14

Mice body weights were recorded twice a week. Lethality and behaviour of animals were recorded every day. All vehicle control mice died between D8 to D10 from peritoneal carcinomatosis associated with ascites. Three (3) mice from group 2 died one day after treatment due to formulation toxicity. The remaining seven (7) died between days 8 and 12. Mice from group 3 died between days 8 and 12. The results are expressed as percent of mean survival time of treated animals over the mean survival time of the control group (treated vs control, T/C %) and as increase life span (mean survival time of treated animals minus that of control animals over the mean survival time of the control group; ILS %). By NCI criteria, T/C exceeding 125% and ILS increasing 25% indicate that the drug has significant anticancer activity.

Compared with vehicle-treated mice, % T/C were 133.3% and 138.9% and ILS 33 and 38.9 for groups 2 and 3, respectively. These results indicate a moderate but significant enhancement of survival time of P388 IP leukemia bearing mice treated with the compound of Formula I.

Example 6

Efficacy of Formula I Against Human PC3 Prostate Cancer Model

The anticancer activity of the compound of Formula I was further tested in a human PC3 prostate model in mice. HRLN male nude mice (8 weeks of age) were implanted with 1 mm³ PC3 tumor fragments subcutaneously (SC) in the right flank. Animals were randomized (ten per group) when tumors reach an average size of 80-120 mg and treatment began according to the table below. For these studies, the compound of Formula I was formulated in 5% ethanol, 5% PEG-400, 15% Polysorbate 80, and 75% of water containing 5% dextrose.

TABLE 2

Dosing Schedules for Groups 1 to 6

| Gr. | N | Agent | Dose (mg/kg) | Concentration mg/mL | Volume (mL/kg) | Route | Schedule |
|---|---|---|---|---|---|---|---|
| 1 | 10 | Cyclophosphamide | 90 | 9 | 10 | IP | qd x5 |
| 2 | 10 | D5W | — | — | 5 | SC | 5/2/5/2/5 |
| 3 | 10 | Formula I | 30 | 6 | 5 | SC | 5/2/5/2/5 |
| 4 | 10 | Formula I | 50 | 10 | 5 | SC | q3d x7 |
| 5 | 10 | Formula I | 30 | 6 | 5 | IP | q3d x7 |
| 6 | 10 | Formula I | 100 | 10 | 10 | IV | 5/2/5/2/5 |

Tumor measurements were taken twice weekly using callipers and were converted to tumor mass (in milligrams) using the formula: with² (mm)×length (mm)×0.52. Body weights were also recorded twice weekly. Statistical analysis was done using the unpaired two-tailed Student's t test.

% T/C was calculated at day 38 once animals in the control group had to be sacrificed due to tumor burden. Bolus intravenous treatment did not result in activity (likely due to short half-life and lack of sustaining therapeutically effective drug levels). On the other hand, bolus subcutaneous administration at 30 mg/kg given from days 1 to 5, 8 to 12 and 15 to 19, or at 50 mg/kg every three days×7 (days 1, 4, 7, 10, 13, 16 and 19) where we maintain drug levels at therapeutically effective drug concentrations for over 8 hours resulted in significant antitumor activity with % T/C of 25.5% and 14.6%, respectively (P<0.0001).

TABLE 1

Survival of mice bearing IP leukemia

| Grp | Treatment | Schedule | Mean Survival Days ± SD | Median survival | % T/C | % ILS |
|---|---|---|---|---|---|---|
| 1 | PEG-PG (Vehicle) | IV (D1 & 8) then IP (D2-7 & D9-10) | 9 ± 0.8 | 9 | — | — |
| 2 | Formula I | IV 50 mg/kg (D1), IP 10 mg/kg (D2-4 & D6-12) | 11 ± 1.5 | 12 | 133.3 | 33 |
| 3 | Formula I | IP 10 mg/kg (D1-4 & D8-14) | 12.6 ± 4.9 | 12.5 | 138.9 | 38.9 |

Figure 7:
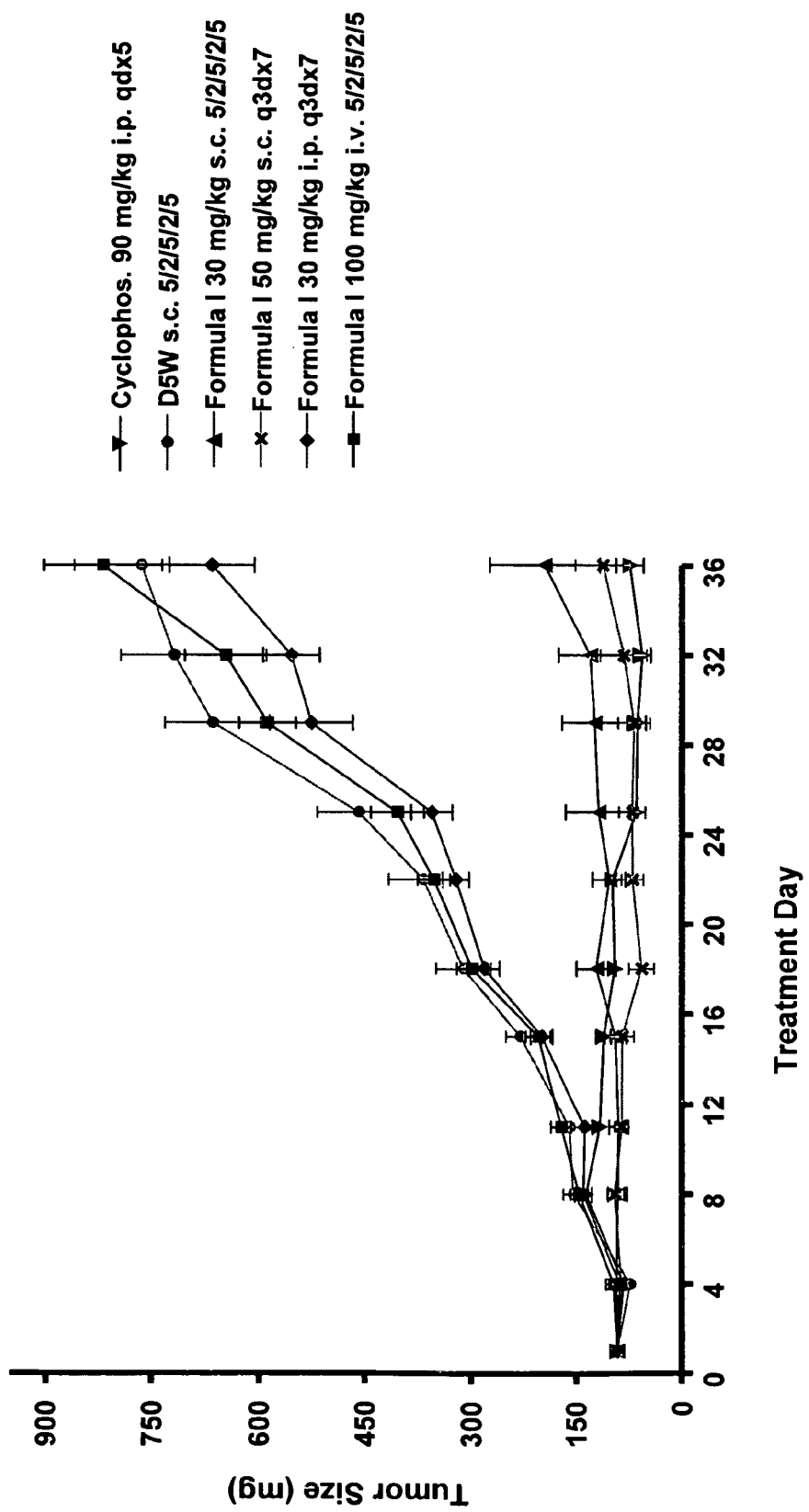
FIG. 7: shows the antitumor efficacy of the compound of Formula I against human prostate tumor (PC3) xenografts in male Harlan nude mice.
Figure 8:
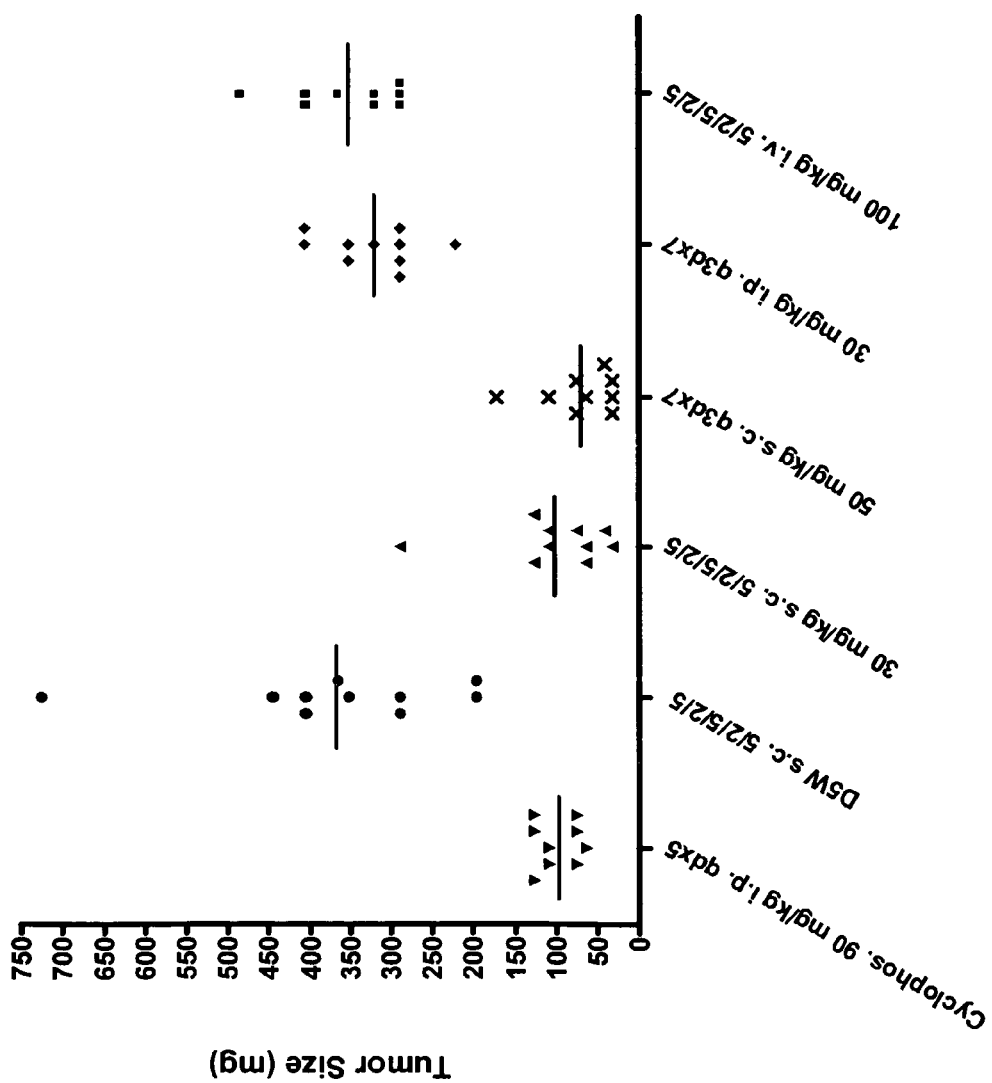
FIG. 8: shows the antitumor efficacy of the compound of Formula I against human prostate tumor (PC3) xenografts on individual male Harlan nude mice at day 22 of treatment.

FIG. 7 shows antitumor efficacy results of the compound of Formula I against human prostate tumor xenografts. FIG. 8 shows antitumor efficacy results on individual animals on the 22$^{nd}$ day of treatment.

Example 7

Efficacy of Formula I Against Human MDA-MB-231 Breast Cancer

The antitumor activity of the compound of Formula I was further tested in a human MD-MB-231 breast cancer model in mice. HRLN female nude mice (8 weeks of age) were treated with 5×10$^6$ MDA-MB-231 tumor cells (SC) in the right flank. Animals were randomized (ten per group) when tumors reach an average size of 80-120 mg and treatment began according to the table below. For these studies, the compound of Formula I was formulated in 5% ethanol, 5% PEG-400, 15% Polysorbate 80, and 75% of water containing 5% dextrose.

TABLE 3

Dosing Schedules for Groups 1 to 8

| Gr | N | Agent | Dose (mg/kg) | Concentration (mg/mL) | Volume (mL/kg) | Route | Schedule |
|---|---|---|---|---|---|---|---|
| 1 | 10 | D5W | — | — | 10 | IV | 5/2/5/2/5 |
| 2 | 10 | paclitaxel | 30 | — | | IV | qod x5 |
| 3 | 10 | Vehicle | — | — | 5 | SC | qd x21 |
| 4 | 10 | Formula I | 100 | 10 | 10 | IV | 5/2/5/2/5 |
| 5 | 10 | Formula I | 30 | 6 | 5 | SC | 5/2/5/2/5 |
| 6 | 10 | Formula I | 20 | 6 | 3.3 | SC | qd x21 |
| 7 | 10 | Formula I | 50 | 10 | 5 | SC | q3d x7 |
| 8 | 10 | Formula I | 30 | 6 | 5 | IP | q3d x 7 |

Tumor measurements were taken twice weekly using calipers and were converted to tumor mass (in milligrams) using the formula: with$^2$ (mm)×length (mm)×0.52. Body weights were also recorded twice weekly. Statistical analysis was done using the unpaired two-tailed Student's t test.

% T/C was calculated at day 21 once animals in the control group had to be sacrificed due to tumor burden. Bolus intravenous treatment did not result in activity (likely due to short half-life and lack of sustaining therapeutically effective drug levels). On the other hand, subcutaneous administration at 20 mg/kg given everyday for 21 days or at 30 mg/kg given from days 1 to 5, 8 to 12 resulted in significant antitumor activity with % T/Cs of 40% and 35% respectively; P<0.0001). Subcutaneous or intraperitoneal administration at 50 and 30 mg/kg respectively every three days×7 (days 1, 4, 7, 10, 13, 16 and 19) were also effective giving moderate but statistically significant T/C values of 68% (P=0.0019) and 58% (P=0.0007).

Figure 9:
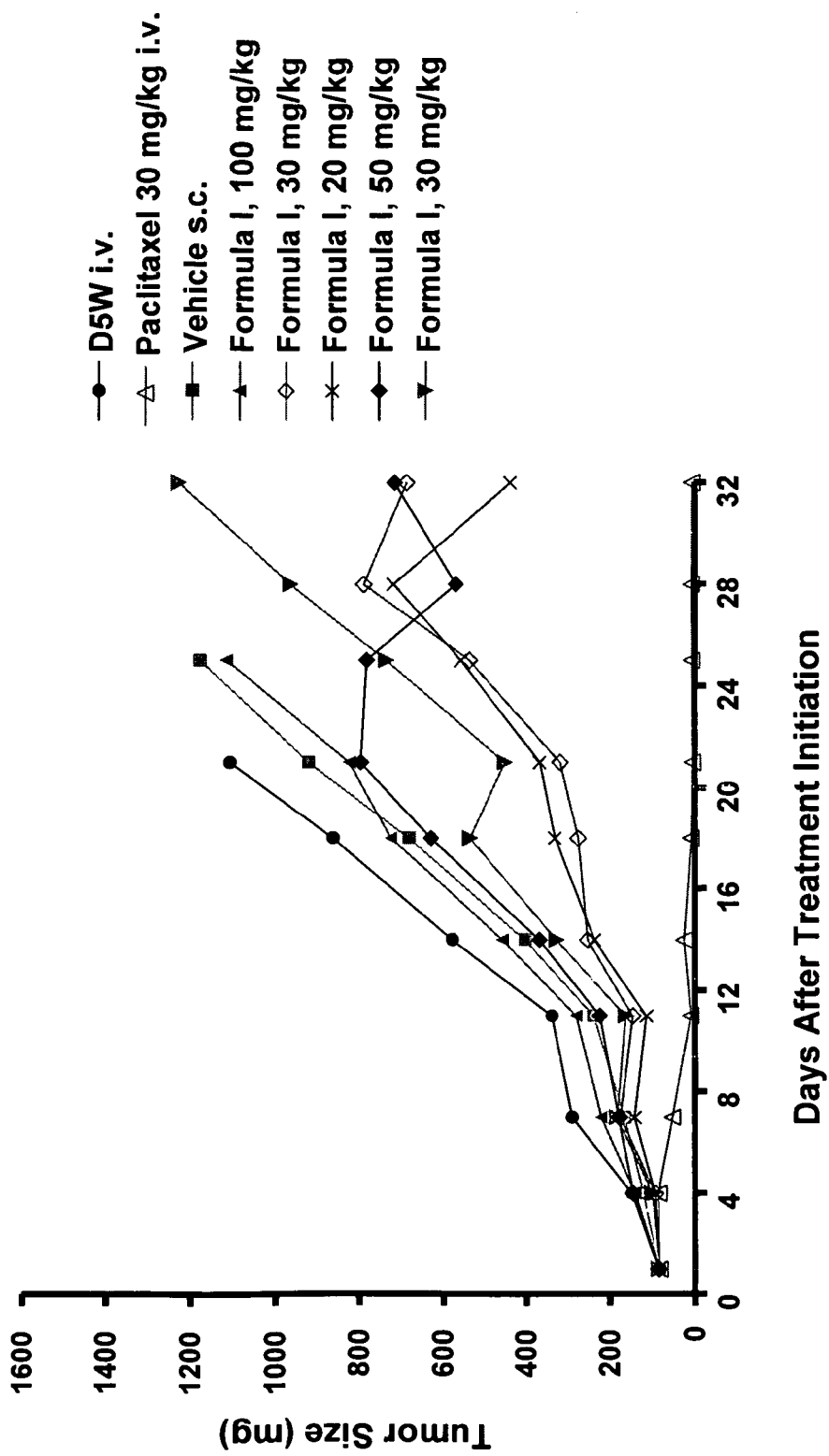
FIG. 9: shows the antitumor efficacy of the compound of Formula I against human breast tumor (MDA-MB-231) xenografts in female Harlan nude mice.
Figure 10:
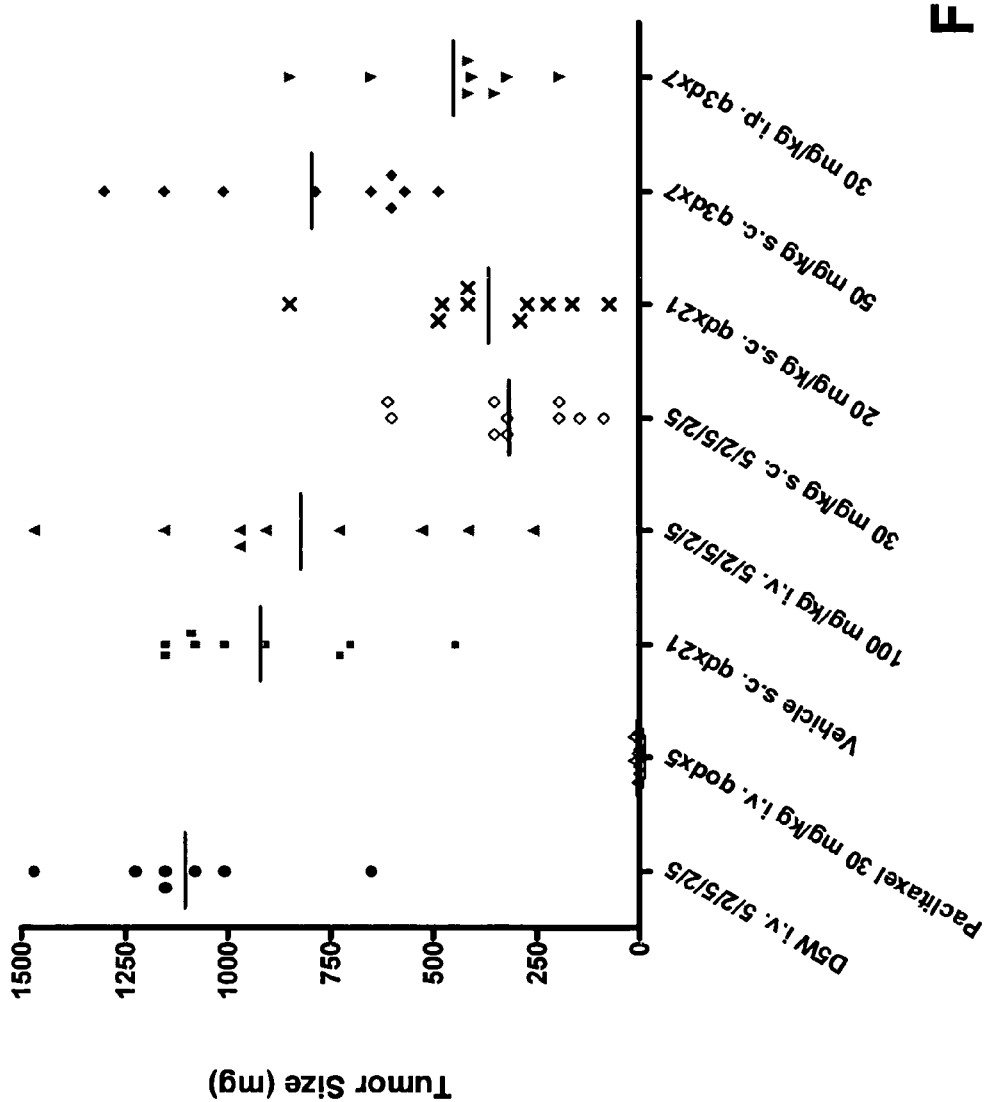
FIG. 10: shows the antitumor efficacy of the compound of Formula I against human breast tumor (MDA-MB-231) xenografts on individual female Harlan nude mice at day 21 of treatment.

FIG. 9 shows antitumor efficacy results of the compound of Formula I against human breast tumor xenografts. FIG. 10 shows antitumor efficacy results on the 21$^{st}$ day of treatment.

Example 8

In Vivo CIV Administration of the Compound of Formula I

Antitumor evaluation of the compound of Formula I against human tumors engrafted into nude mice indicated that antitumor efficacy was dependent on the route of administration. Indeed, while bolus intravenous (IV) administration was better tolerated and higher doses could be administered, it did not result in antitumor-activity. On the other hand, subcutaneous (SC) and intraperitoneal (IP) bolus administrations, while not as well tolerated (IP dosing resulted in some intestinal occlusion and SC dosing in swelling and thickening of the skin), were effective. Maximum tolerated doses in mice for IV, SC and IP bolus administrations are 200 mg/kg, 30 mg/kg and 20 mg/kg, respectively. The pharmacokinetic profile of the compound of Formula I following these different administration routes was thus evaluated.

Following 30 mg/kg bolus IV administration, plasma concentrations of Formula I fell rapidly within one hour from ~425 µM to 1.3 µM ($t_{1/2}$ α of 4.7 min). Four hours after compound administration, the concentration of the compound of Formula I in plasma further decreased to ~0.2 µM and continued to decrease to ~0.1 µM by 8 hours. On the other hand, SC and IP bolus administration resulted in lower but sustained plasma drug concentrations with peak concentrations of 2.3 µM and 7.8 µM reached after 1 h and 15 min, respectively. The plasma concentration of Formula I remained at approximately 1.8 µM and 0.95 µM for up to 8 hours. In xenograft antitumor studies, daily bolus administrations of 30 mg/kg (SC) or 20 mg/kg (IP), which are shown to results in sustained plasma concentrations of ~1-2 µM, are effective. Peak concentrations (Cmax) attained for the 30 mg/kg bolus IV administration was significantly higher, yet due to the rapid initial decline, Formula I plasma concentrations would not be sustained at a target drug concentration of ~1-2 µM for more than one hour.

These PK data can explain why bolus IV administration was not effective in producing tumor growth inhibition. The antitumor activity of Formula I is thus dependent on sustained plasma concentrations approaching the average in vitro IC$_{50}$ values of ≧1 µM against tumor cell lines, rather than high $C_{max}$ levels followed by rapid elimination. The ability to remain above this "therapeutic threshold" of ≧1 µM for extended periods of time is preferred for obtaining antitumor efficacy.

Neoplastic drugs administered by infusion are normally administered as short bolus infusions (30 min for up to 8 h). Since preclinical evaluation of Formula I indicated that sustained and prolonged exposure (up to two weeks) is required for antitumor activity, and intraperitoneal and subcutaneous administrations are not suitable for anticancer treatment in humans, continuous intravenous infusion was evaluated for PK profile and toxicity in rats and monkeys.

a) In Vivo Pharmacokinetics of Formula I Given CIV in Rats:

Sprague-Dawley rats received an intravenous continuous infusion over 14 days of Formula I at 25 mg/kg/day, 50 mg/kg/day, or 75 mg/kg/day at a rate of 2 mL/kg/h for 14 consecutive days (same formulation as in Example 7). Blood was collected from the jugular vein in tubes containing K$_2$ EDTA from 3 rats/sex/group at the following time points: 2, 6, and 12 hours after the start of dosing on Day 1, on Day 2 at 6 hours (approximately 30 hours after the start of dosing), on Days 6 and 10 at 6 hours, and on Day 15, 1 hour prior the end of dosing, and then at 5 min, 15 min, 30 min, 1 h, and 2 h after the end of dosing.

Figure 11:
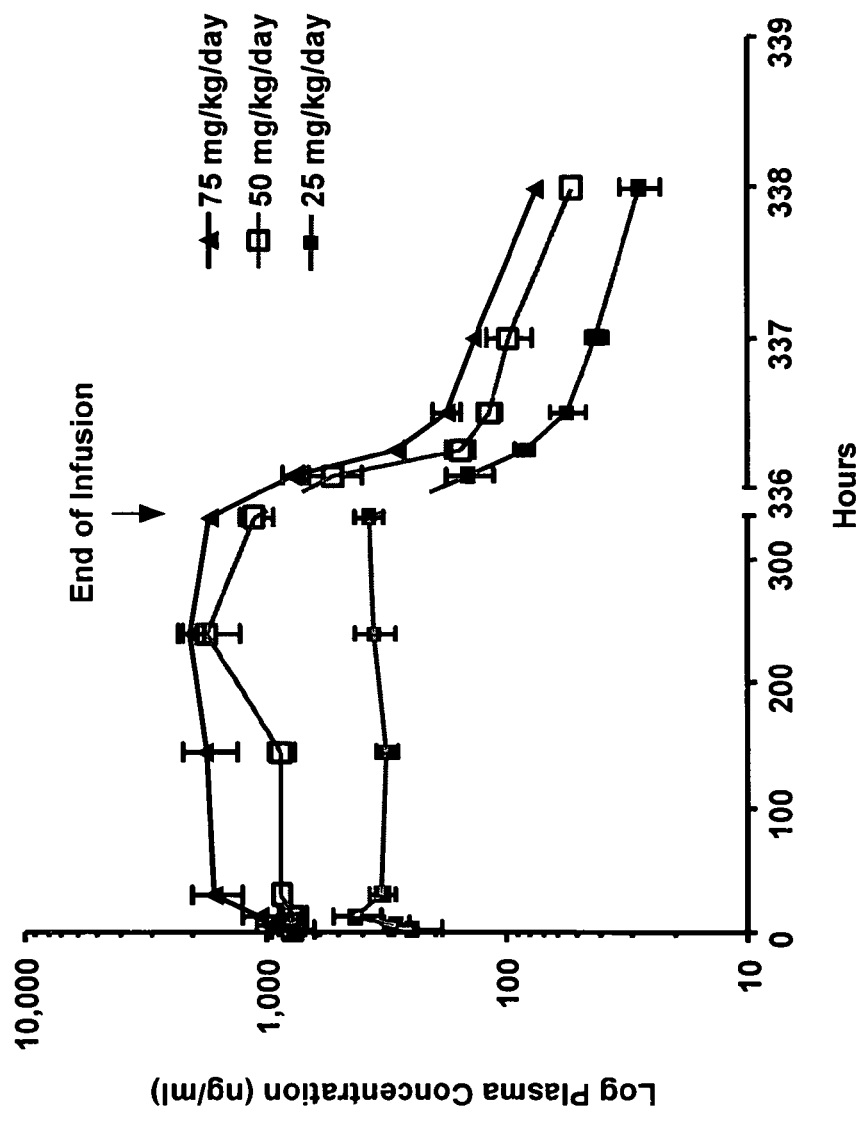
FIG. 11: shows the mean (±SD) plasma concentrations, during and post-infusion, of the compound of Formula I in Sprague-Dawley rats when administered continuous intravenous infusion (CIV) for 14 days (336 hours) at a dosage of 25 mg/kg/day, 50 mg/kg/day, and 75 mg/kg/day.

Results from this 14-day IV continuous infusion of Formula I are shown in Table 4 and FIG. 11. For the groups that received 25 mg/kg/day or 75 mg/kg/day, steady-state Formula I plasma concentrations were observed throughout the 14-day CIV infusion, with steady-state plasma concentrations of 347 ng/mL (~0.8 µM) and 1,796 ng/mL (~3.9 µM), respectively. For the mid dose group of 50 mg/kg/day, Formula I plasma concentration was unusually high on Day 10 (1,753 ng/mL or ~3.8 µM) and decreased back to the steady-state level at Day 14 as measured during prior measurements (1,150 ng/mL or ~2.5 μM), suggesting possible analytical or biological variability. Mean steady-state plasma concentrations in the 50 mg/kg/day and 75 mg/kg/day groups exceeded the therapeutic threshold of 2 μM defined in the in vivo antitumor activity experiments throughout the 14-day infusion period, with concentrations of ~2.5 ~M and ~3.9 μM, respectively. AUCs for the different groups increased with increasing dose level, but this increase was slightly greater than dose-proportional with an AUC of 116,418 ng/mL*h for the 25 mg/kg/day group, 396,134 ng/mL*h for the 50 mg/kg/day group, and finally 597,378 ng/mL*h for the 75 mg/kg/day group. When infusion of Formula I in the different groups was terminated, rapid elimination of Formula I from plasma was observed in all groups, showing that Formula I is rapidly cleared from plasma. At 2 hours after the end of infusion of Formula I, the mean concentration of Formula I had declined to 28 ng/mL in the low dose group (25 mg/kg/day), 53 ng/mL in the mid dose group (50 mg/kg/day), and to 75 ng/mL for the high dose group (75 mg/kg/day). The $T_{1/2}z$ for Formula I varied between 1.2 and 1.6 h for the different dosage groups.

TABLE 4

PK Results in rats from a Formula I 14-day CIV infusion

| Dose (mg/kg/day) | Css (ng/mL)[a] | $AUC_\alpha$ (ng/mL * h) | CL (L/h/kg) | Vss (L/kg) | Vz (L/kg) | $T_{1/2}z$ (h)[b] |
|---|---|---|---|---|---|---|
| 25 | 347 | 116,418 | 3.0 | 15.8 | 6.8 | 1.6 |
| 50 | 1,150 | 396,134 | 1.8 | 38.8 | 3.1 | 1.2 |
| 75 | 1,796 | 597,378 | 1.8 | 15.4 | 3.1 | 1.2 |

[a]Average of plasma concentration between 30 h and 14 days.
[b]Calculated at the end of treatment In summary, the results showed that steady-state Formula I plasma concentrations above the therapeutic threshold of 2 μM were obtained with a 14-day IV continuous infusion of Formula I in rats at doses of 50 and 75 mg/kg/day. When dosing of Formula I was terminated after 14 days, the drug was rapidly eliminated from the plasma of rats for all dosing groups.

b) In Vivo Pharmacokinetics of Formula I Given CIV in Monkeys:

Cynomolgus monkeys received continuous IV infusion over 14 days of Formula I at 5 mg/kg/day, 15 mg/kg/day, or 30 mg/kg/day. The drug was infused intravenously (24 hours/day) into the femoral vein at a dose rate of 2 ml/kg/hour for 14 consecutive days. Blood samples were removed from each monkey on Days 1, 2, 6, 10, and 15 of the treatment period. Monkeys were bled by venipuncture and samples were collected into tubes containing $K_2EDTA$. On Day 1, samples were collected at 2, 6, and 12 hours after initiation of treatment. Additional samples were collected at 30 hours after the start of infusion (Day 2). On Days 6 and 10, samples were collected at approximately 6 hours after the bag changes. At the end of the 14 days of infusion, on Day 15, samples were collected at 1 hour prior to cessation of dose administration, and at 5 min, 30 min, 1 h, 2 h, 4 h, 8 h, and 24 h following cessation of dose administration.

Figure 12:
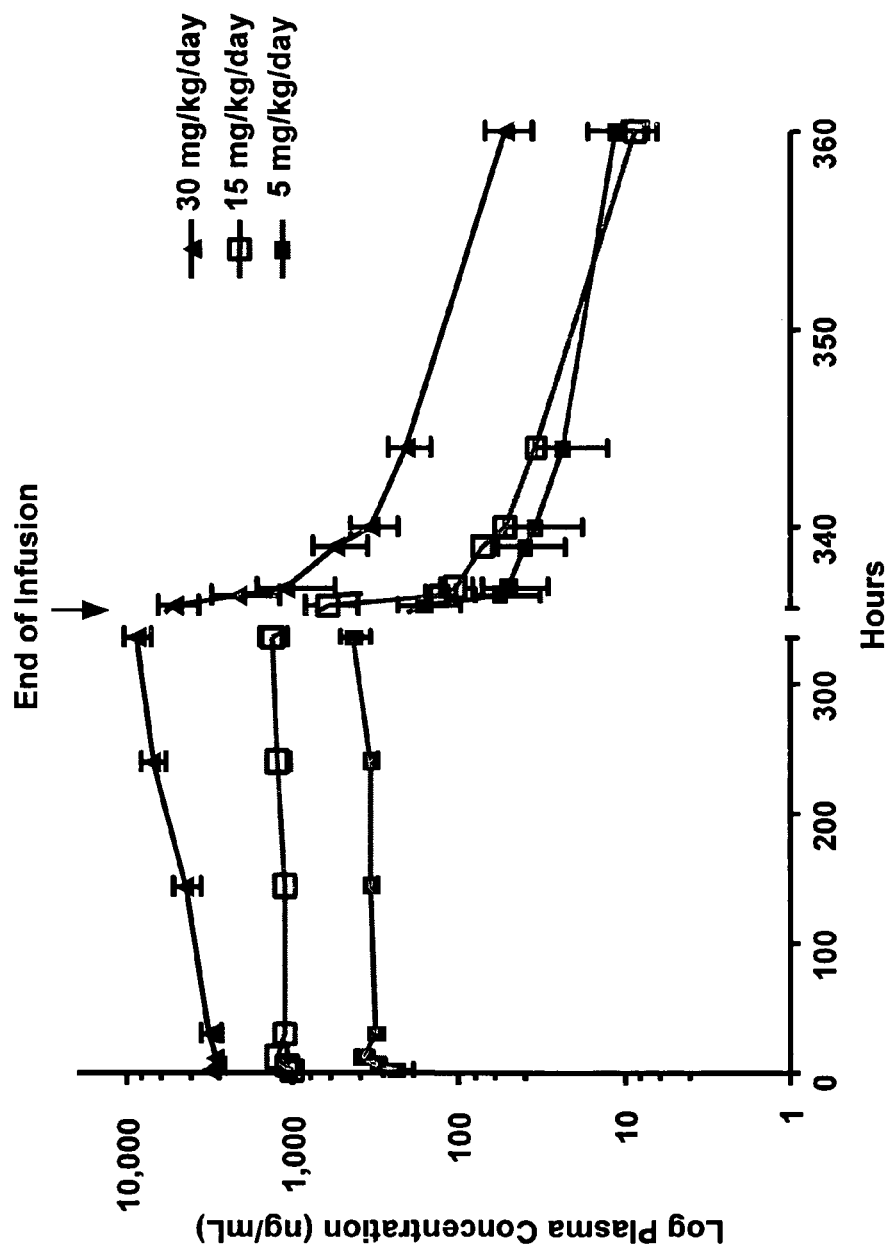
FIG. 12: shows the mean (±SD) plasma concentrations, during and post-infusion, of the compound of Formula I in Cynomolgus monkeys when administered CIV for 14 days (336 hours) at a dosage of 5 mg/kg/day, 15 mg/kg/day, and 30 mg/kg/day.

Results from this 14-day IV continuous infusion of Formula I are shown in Table 5 and FIG. 12. For the groups that received a 5 mg/kg/day dose or 15 mg/kg/day, steady-state Formula I plasma concentrations were observed throughout the 14-day CIV infusion, with mean steady-state plasma concentrations (between 30 h and 14 days) of 358 ng/mL (~0.8 μM) and 1,173 ng/mL (~2.5 μM), respectively. For the high dose group of 30 mg/kg/day, Formula I plasma concentration increased throughout the 14-day infusion period from 2,814 ng/mL (~6.1 μM) at Day 1 to 4,354 ng/mL (~9.4 μM) at Day 6, to 6,855 ng/mL (~15 μM) by Day 10, and to 8,561 ng/mL (~18.5 μM) by day 15. Plasma concentrations in the 15 mg/kg/day and the 30 mg/kg/day groups exceeded the therapeutic threshold observed in the in vivo antitumor activity experiments throughout the 14-day infusion period. AUCs for the different groups increased approximately proportionally to the dose received between the low and middle dose groups, with a mean AUC of 119,018 ng/mL*h for the 5 mg/kg/day group, 400,116 ng/mL*h for the 15 mg/kg/day group (3.4-fold increase between the groups, which is proportional to the 3-fold increase in dose level). However, the AUC value for the high dose group (30 mg/kg/day) was markedly greater, i.e. 1,874,950 ng/mL*h, which is 4.7-fold higher than that of the middle dose group, despite the 2-fold increase in dose level. When infusion of Formula I in the different groups was terminated, rapid elimination of the compound of Formula I from plasma was observed in all groups. The $T_{1/2}z$ for the compound of Formula I varied between 8.1 and 11.5 h for the different dosage groups.

TABLE 5

PK Results in monkeys from a Formula I 14-day CIV infusion

| Dose (mg/kg/day) | Css (ng/mL)[a] | $AUC_\alpha$ (ng/mL * h) | CL (L/h/kg) | Vss (L/kg) | Vz (L/kg) | $T_{1/2}z$ (h)[c] |
|---|---|---|---|---|---|---|
| 5 | 358[b] (85) | 119,018 (26,690) | 0.61 (0.14) | 7.1 (3.9) | 10 (3) | 12 (3) |
| 15 | 1,173 (340) | 400,116 (126,140) | 0.56 (0.13) | 3.6 (2.0) | 6.8 (2.9) | 8.3 (2.2) |
| 30 | 6,283 (3,650) | 1,874,950 (945,067) | 0.27 (0.11) | 10.7 (6.2) | 3.2 (1.7) | 8.1 (1.0) |

[a]Average of plasma concentration between 30 h and 14 days.
[b]Values are Mean (SD).
[c]Calculated at the end of treatment In summary, the results showed that stable Formula I plasma concentrations above the therapeutic threshold of 2 μM are obtained with a 14-day IV continuous infusion of Formula I in monkeys. When dosing of Formula I was terminated after 14 days, the drug was rapidly eliminated from the plasma of monkeys for all dosing groups.

c) In Vivo Toxicity of Formula I in Rats and Monkeys:

When administered as a 14-day continuous intravenous infusion (as in b), no severe compound associated toxicity was observed in monkeys, and side effects, including inappetance and a moderate degree of regenerative anemia, were reversible. Diffuse vacuolization of hepatocytes and accumulation of foamy histiocytes (macrophages) in the spleen were observed in monkeys, which reflected clearance of the vehicle used. No degenerative changes were observed in any organs, including the infusion site, and there were no effect on body weight, ocular condition, electrocardiographic activity and other parameters assessed in the monkeys.

In the rats, a 14-day infusion (as in a) was associated with necrotization and inflammatory lesions at the site of infusion for all treated and control groups. The toxicity was due to the vehicle and was attributed to smaller size of infusion vessels, and concurrent catheter tract infection.

Single bolus intravenous administration showed an MTD of 85 mg/kg in healthy rats, and an MTD of about 35 mg/kg in monkeys.

Acute toxicity was also evaluated in a 24-hour CIV administration schedule in monkeys and doses of 35 mg/kg and 70 mg/kg, for a period of 24 hours (infusion rate of 2 mL/kg/hour), were both well tolerated.

Example 9

Simulation of the Pharmacokinetics of Formula I in Humans

An analysis was performed to derive allometric equations for Formula I pharmacokinetic parameters using Formula I plasma concentration-time data from three species, including mouse, rat, and monkey, and to estimate human pharmacokinetic parameters from those allometric equations.

Plasma concentrations of Formula I were obtained from mice, rats, and monkeys following intravenous injection or continuous infusion. Formula I pharmacokinetic parameters in mice, rats, and monkeys were estimated using population pharmacokinetic analysis, a function of the software program NONMEM™ (version 5). Typical population pharmacokinetic parameters for Formula I in humans were extrapolated from allometric equations that were derived from pharmacokinetic parameters estimated in the three animal species. Formula I plasma concentration-time profiles following 9-day or 14-day continuous infusion were simulated in a patient (weight, 70 kg; BSA, 1.8 m$^2$) with a typical population clearance (mean CL), 50% higher clearance (mean CL+50%× mean CL), and 50% lower clearance (mean CL−50%×mean CL), respectively.

A two-compartment model with a first-order elimination from the central compartment adequately described Formula I plasma concentration-time profiles following intravenous bolus injection (30 mg/kg) in mice and rats, 7-day continuous infusion in rats (50 to 170 mg/kg/day), and 14-day continuous infusion in monkeys (5 to 30 mg/kg/day). The estimated population pharmacokinetic parameters of Formula I in mice, rats, and monkeys are presented in Table 6.

TABLE 6

Typical Population Pharmacokinetic Parameters in Mouse, Rat, Monkey, and Estimated Parameters in Humans[a]

|  | WT (Kg) | V1 (L/kg) | V2 (L/kg) | Q (L/h/kg) | Ke (h$^{-1}$) | CL (L/h/kg) | Vss (L/kg) | $t_{1/2},\alpha$ (h) | $t_{1/2},\beta$ (h) |
|---|---|---|---|---|---|---|---|---|---|
| Mouse (IV) | 0.022 | 0.176 | 0.225 | 0.0654 | 8.466 | 1.49 | 0.401 | 0.078 | 2.49 |
| Rat (IV + CIV) | 0.225 | 0.126 | 0.236 | 0.0696 | 8.651 | 1.09 | 0.362 | 0.075 | 2.50 |
| Monkey (CIV) | 3.8 | 0.203 | 0.419 | 0.0398 | 2.172 | 0.441 | 0.622 | 0.308 | 8.05 |
| Human | 70 | 0.198 | 0.559 | 0.032 | 1.192 | 0.236 | 0.757 | 0.509 | 13.8 |
|  | WT (Kg) | V1 (L) | V2 (L) | Q (L/h) |  | CL (L/h) | Vss (L) |  |  |
| Mouse (IV) | 0.022 | 0.004 | 0.005 | 0.001 | — | 0.032 | 0.009 | — | — |
| Rat (IV + CIV) | 0.225 | 0.028 | 0.053 | 0.016 | — | 0.245 | 0.081 | — | — |
| Monkey (CIV) | 3.8 | 0.771 | 1.59 | 0.151 | — | 1.68 | 2.360 | — | — |
| Human | 70 | 13.9 | 39.2 | 2.27 | — | 16.5 | 53.1 | — | — |

[a]Population pharmacokinetic parameters for Formula I in humans were estimated from allometric equations derived from three species mouse, rat, and monkey.

A 14-day continuous infusion in monkeys resulted in mean steady-state plasma concentrations of 0.75, 2.57, and 14.07 µM at dose levels of 5, 15, and 30 mg/kg/day, respectively, and corresponding mean clearance values of 0.63, 0.57, and 0.23 Uh/kg, respectively. Application of a two-compartment model with Michaelis-Menten elimination better described the concentration data in monkeys than the linear model. Because the target concentration in humans is 2 µM, at which linear pharmacokinetics is assumed, all simulations for human plasma concentrations were performed based on a two-compartment model with linear first-order elimination.

Figure 13:
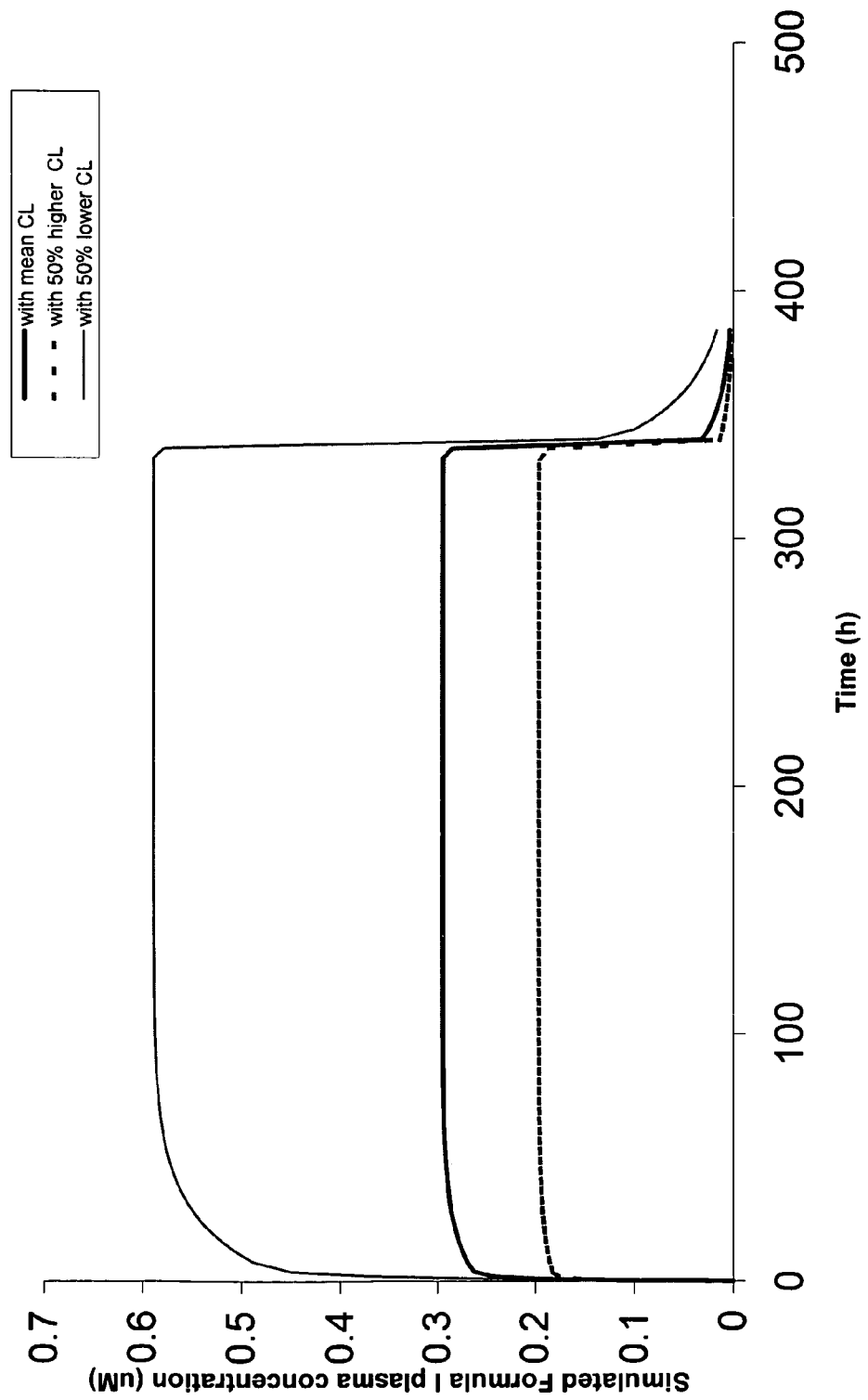
FIG. 13: shows a simulated Formula I plasma concentration-time profiles in humans, following a CIV infusion at 30 mg/m$^2$/day for 14 days.

Allometric equations for the pharmacokinetic parameters clearance (CL), volume of distribution (V1 and V2), and inter-compartmental clearance (Q) were derived. The population PK parameters of the compound of Formula I for humans were extrapolated from the allometric equations, and the estimated values are shown in Table 6. Simulated Formula I plasma concentration-time profiles in humans are shown in FIG. 13 and estimated end of infusion concentrations are provided in Table 7.

TABLE 7

Projected Formula I Steady-state Concentrations Following CIV Infusion in Humans

| | Dose (mg/m²/day) | Estimated Formula I Plasma Concentration$^a$ (µM) | | |
|---|---|---|---|---|
| | | Typical Population Clearance | 50% Higher Clearance | 50% Lower Clearance |
| CIV | 30 | 0.29 | 0.20 | 0.59 |
| (For 14 days) | 60 | 0.59 | 0.40 | 1.2 |
| | 120 | 1.2 | 0.79 | 2.4 |
| | 180 | 1.8 | 1.2 | 3.5 |

$^a$Formula I concentrations were estimated for a patient (70 kg, BSA 1.8 m²) with typical mean population pharmacokinetic parameters (CL, 0.236 L/h/kg; V1, 0.198 L/kg; V2, 0.559 L/kg; Q, 0.032 L/h/kg), a patient with 50% lower CL than the typical mean value (0.118 L/h/kg), and a patient with 50% higher CL than the typical mean value (0.354 L/h/kg).

From the simulation of a 14-day continuous infusion of the compound of Formula I at a dose of 30 mg/m²/day, the estimated steady-state plasma concentration, using parameters of an average patient, was 0.29 µM (Table 7). We have observed in the pharmacokinetic profiling of the compound of Formula I in monkeys that, in a 14-day continuous IV infusion, at doses of 5 mg/kg/day and 15 mg/kg/day, steady-state Formula I plasma concentrations were observed throughout the 14-day CIV infusion. It can thus be anticipated that dosing of the compound of Formula I at 180 mg/m²/day (4.5 mg/kg/day) in humans will produce steady-state plasma concentrations of the compound of Formula I during a continuous IV infusion over 14 days.

Example 10

Administration of the Compound of Formula I to Humans

The compound of Formula I is administered to humans for the treatment of cancer. The product is formulated (bulk formulation) as follows:

| Ingredient: | % wt |
|---|---|
| Formula I | 3.15 |
| Polysorbate 80 | 55.16 |

-continued

| Ingredient: | % wt |
|---|---|
| PEG 400 | 15.76 |
| Ethanol absolute | 12.45 |
| Water | 12.45 |
| (+)-Sodium L-ascorbate | 1.04 |

The bulk formulation is reconstituted in sterile 0.9 saline prior to patient administration. Bulk formulation vials are provided with a drug reconstitution kit consisting of a sterile 60 mL pre-filled syringe containing 52 mL of 0.9% saline, infusion bag, and administration set (with pump connector) and extension set. The extension set comprises an anti-siphon valve and a sterile 0.2 micron in-line filter. The vial content is diluted with 52 mL of sterile 0.9% saline with the aid of a pre-filled syringe. This overfill ensures that there is a minimal extractable premix volume of 59 mL containing 4.48 mg/mL Formula I, which corresponds to 265 mg/vial. The dosing formulation is isotonic at this drug concentration in 0.9% saline.

Depending on the dose to administer, the dosing formulation is then transferred to a 250-mL, 500-mL, or 1-L EVA or PP infusion bag. The infusion bag is connected to a CADD Prizm VIP 6101 model pump for continuous 24-hour infusion. The daily dose is adjusted with the flow rate of the pump, which is programmed and locked by the pharmacist. Patient is monitored for adverse side effects and efficacy of the treatment.

For example, a 180 mg/m² daily dose is given during a period of 14 days to a human patient having a 1.8 m² body surface area. The patient is administered daily volume of about 72.34 mL (324.1 mg of drug), for a total of 1012.8 mL (4537.4 mg of drug) of the reconstituted formulation above at a flow rate adjusted to about 3.014 mL/h. The 14-day infusion is given in two 7-day infusions, i.e. changing infusion bag after 7 days, each bag administering a total volume of about 506.4 mL. The patient is then allowed to rest for 7 days. One or more additional 14-day infusion treatments are given in the same manner, with or without adjustment of the dosage, depending on response and adverse side effects.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:

1. A method of inhibiting the growth or proliferation of a neoplastic cell in a mammal, comprising administering by continuous intravenous infusion a therapeutically effective amount of a compound of Formula I or a pharmaceutical acceptable prodrug thereof:

Formula I such that the growth or proliferation of the neoplastic cell is inhibited, wherein the neoplastic cell is a cell of a solid neoplasm selected from the group consisting of pancreatic cancer, prostate cancer, colorectal cancer, lung cancer, central nervous system cancer, ovarian cancer, melanoma, breast cancer, renal cancer and liver cancer, or a cell of a hematopoietic neoplasm selected from the group consisting of leukemia and a lymphoma.

2. The method of claim 1, wherein said continuous intravenous infusion is administered for at least 8 hours per day for a period of 1 to 28 days.

3. The method of claim 2, wherein said continuous intravenous infusion is administered 24 hours per day for a period of 1 to 28 days.

4. The method of claim 3, wherein said continuous intravenous infusion is administered 24 hours per day for a period of 7 to 14 days.

5. The method of claim 1, wherein the central nervous system cancer is selected from the group consisting of glioblastoma, neuroblastoma, gliosacaroma, astrocytoma and oligodendroglioma.

6. The method of claim 5, wherein said central nervous system cancer is glioblastoma.

7. The method of claim 1, wherein said solid neoplasm is prostate cancer.

8. The method of claim 1, wherein said solid neoplasm is breast cancer.

9. A method for the administration of a compound of Formula I:

Formula I in a mammal having a neoplasm, comprising administering a therapeutically effective amount of the compound of Formula I by continuous intravenous infusion, for a period at least 8 hours per day, for 1 to 28 days, wherein said amount is sufficient to inhibit growth of the neoplasm, and wherein the neoplasm is a solid neoplasm selected from the group consisting of pancreatic cancer, prostate cancer, colorectal cancer, lung cancer, central nervous system cancer, ovarian cancer, melanoma, breast cancer, renal cancer and liver cancer, or a hematopoietic neoplasm selected from the group consisting of leukemia and a lymphoma.

10. The method of claim 9, wherein said continuous intravenous infusion is administered 24 hours per day for a period of 1 to 28 days.

11. The method of claim 10, wherein said continuous intravenous infusion is administered 24 hours per day for a period of 7 to 14 days.

12. The method of claim 9, wherein the central nervous system cancer is selected from the group consisting of glioblastoma, neuroblastoma, gliosacaroma, astrocytoma and oligodendroglioma.

13. The method of claim 9, wherein said solid neoplasm is prostate cancer.

14. The method of claim 9, wherein said solid neoplasm is breast cancer.

15. The method of claim 12, wherein said central nervous system cancer is glioblastoma.

16. The method of claim 10 wherein the compound of Formula I is administered at about 10 to about 1000 mg/m$^2$ of body surface of the mammal per day.

17. The method of claim 10, wherein the compound of Formula I is administered at about 20 to about 750 mg/m$^2$ of body surface per day.

18. The method of claim 10, wherein the compound of Formula I is administered at about 30 to about 500 mg/m$^2$ of body surface per day.

19. The method of claim 10, wherein the compound of Formula I is administered at about 120 to about 480 mg/m$^2$ of body surface per day.

20. The method of claim 9, wherein said mammal is a human.

21. A method of treating a neoplastic condition in a mammal, comprising administering a therapeutically effective amount of a compound of Formula I:

Formula I by continuous intravenous infusion, administered for at least 8 hours per day over a period of 1 to 28 days, wherein the neoplastic condition is a solid neoplasm selected from the group consisting of pancreatic cancer, prostate cancer, colorectal cancer, lung cancer, central nervous system cancer, ovarian cancer, melanoma, breast cancer, renal cancer, and liver cancer, or a hematopoietic neoplasm selected from the group consisting of leukemia and a lymphoma.

22. The method of claim 21, wherein said continuous intravenous infusion is administered 24 hours per day for a period of 1 to 28 days.

23. The method of claim 22, wherein said continuous intravenous infusion is administered 24 hours per day for a period of 7 to 14 days.

24. The method of claim 21, wherein the central nervous system cancer is selected from the group consisting of glioblastoma, neuroblastoma, gliosacaroma, astrocytoma and oligodendroglioma.

25. The method of claim 21, wherein said solid neoplasm is prostate cancer.

26. The method of claim 21, wherein said solid neoplasm is breast cancer.

27. The method of claim 24, wherein said central nervous system cancer is glioblastoma.

28. The method of claim 22 wherein the compound of Formula I is administered at about 10 to about 1000 mg/m² of body surface of the mammal per day.

29. The method of claim 22, wherein the compound of Formula I is administered at about 20 to about 750 mg/m² of body surface per day.

30. The method of claim 22, wherein the compound of Formula I is administered at about 30 to about 500 mg/m² of body surface per day.

31. The method of claim 22, wherein the compound of Formula I is administered at about 120 to about 480 mg/m² of body surface per day.

32. The method of claim 21, wherein said mammal is a human.

33. A commercial package comprising the compound of Formula I:

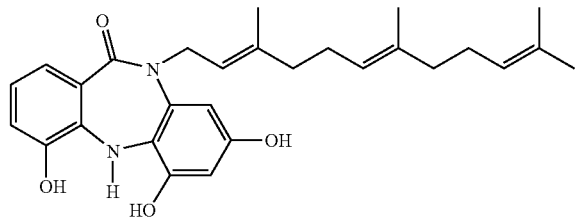

formulated as a preparation for continuous intravenous infusion delivery at least 8 hours per day, for a period of 1 to 28 days, and a written matter describing instructions for the continuous intravenous infusion of the compound of formula I for treating a neoplastic disorder in a mammal, wherein the neoplastic disorder is caused by a solid neoplasm selected from the group consisting of pancreatic cancer, prostate cancer, colorectal cancer, lung cancer, central nervous system cancer, ovarian cancer, melanoma, breast cancer, renal cancer, and liver cancer, or a hematopoietic neoplasm selected from the group consisting of leukemia and a lymphoma.

34. The commercial package of claim 33, wherein said compound of Formula I is formulated as a preparation for continuous intravenous infusion delivery 24 hours per day, for a period of 7 to 14 days.

35. The commercial package of claim 33, wherein the central nervous system cancer is selected from the group consisting of glioblastoma, neuroblastoma, gliosarcoma, astrocytoma and oligodendroglioma.

36. The commercial package of claim 33, wherein said solid neoplasm is prostate cancer.

37. The commercial package of 33, wherein said solid neoplasm is breast cancer.

38. The commercial package of claim 35, wherein said central nervous system cancer is glioblastoma.

39. The commercial package of claim 34 wherein the compound of Formula I is formulated for administration at about 10 to about 1000 milligrams per square meter (mg/m²) of body surface of the mammal per day.

40. The commercial package of claim 34 wherein the compound of Formula I is formulated for administration at about 20 to about 750 milligrams per square meter (mg/m²) of body surface per day.

41. The commercial package of claim 34 wherein the compound of Formula I is formulated for administration at about 30 to about 500 milligrams per square meter (mg/m²) of body surface per day.

42. The commercial package of claim 34 wherein the compound of Formula I is formulated for administration at about 120 to about 480 milligrams per square meter (mg/m²) of body surface per day.

43. The commercial package of claim 33, wherein the mammal in a human.

44. The commercial package of claim 43, further comprising a container suitable for use with an infusion pump.

45. The commercial package of claim 44, wherein the container is an infusion bag.

46. The commercial package of claim 45, wherein the infusion bag is an ethyl vinyl acetate (EVA) or polypropylene (PP) infusion bag.

47. The commercial package of claim 46, further comprising an infusion pump.

48. The method of claim 1, wherein said mammal is a human.

* * * * *